United States Patent
Kiji et al.

(10) Patent No.: US 9,096,534 B2
(45) Date of Patent: Aug. 4, 2015

(54) PYRIDAZINONE COMPOUND AND USE THEREOF

(71) Applicant: SUMITOMO CHEMICAL COMPANY, LIMITED, Tokyo (JP)

(72) Inventors: Toshiyuki Kiji, Hyogo (JP); Takafumi Fusaka, Hyogo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/596,895

(22) Filed: Jan. 14, 2015

(65) Prior Publication Data

US 2015/0126739 A1    May 7, 2015

Related U.S. Application Data

(60) Division of application No. 13/426,894, filed on Mar. 22, 2012, now Pat. No. 8,962,625, which is a continuation of application No. 12/225,233, filed as application No. PCT/JP2007/055579 on Mar. 13, 2007, now Pat. No. 8,541,414.

(30) Foreign Application Priority Data

Mar. 17, 2006  (JP) .................. 2006-074190
Oct. 25, 2006  (JP) .................. 2006-289735

(51) Int. Cl.
C07D 237/16   (2006.01)
A01N 43/58    (2006.01)

(52) U.S. Cl.
CPC .............. C07D 237/16 (2013.01); A01N 43/58 (2013.01)

(58) Field of Classification Search
None
See application file for complete search history.

(56) References Cited

U.S. PATENT DOCUMENTS

| | | | |
|---|---|---|---|
| 5,097,028 | A | 3/1992 | Weissmüller et al. |
| 6,307,047 | B1 | 10/2001 | Black et al. |
| 8,541,414 | B2 | 9/2013 | Kiji et al. |
| 2010/0286390 | A1 | 11/2010 | Shigeta et al. |
| 2011/0003692 | A1 | 1/2011 | Lehr et al. |

FOREIGN PATENT DOCUMENTS

| | | |
|---|---|---|
| CA | 2 474 239 | 7/2003 |
| EP | 0 075 436 | 9/1982 |
| JP | 3-58974 | 3/1991 |
| JP | 11-152273 | 6/1999 |
| WO | 03/059891 | 7/2003 |
| WO | 2005/007632 | 1/2005 |
| WO | 2005/077914 | 8/2005 |
| WO | 2005/077915 | 8/2005 |
| WO | 2006/052962 | 5/2006 |
| WO | 2007/119434 | 10/2007 |

OTHER PUBLICATIONS

International Search Report dated Aug. 8, 2007 in the International (PCT) Application PCT/JP2007/055579.
International Preliminary Report on Patentability together with English translation of PCT Written Opinion dated Sep. 23, 2008 in the International (PCT) Application PCT/JP2007/055579.
Thomas M. Stevenson et al., "Application of Cross-Coupling and Metalation Chemistry of 3(2H)-Pyridazinones to Fungicide and Herbicide Discovery", J. Heterocyclic Chem., 42, pp. 427-435, Apr. 2005.
Bert U. W. Maes et al., "Suzuki reactions on chloropyridazinones: an easy approach towards arylated 3(2H)-pyridazinones", Tetrahedron, 57, pp. 1323-1330, 2001.
Zsuzsanna Riedl et al., "Synthesis of new pyridazino[4,5-c]isoquinolinones by Suzuki cross-coupling reaction", Tetrahedron, 58, pp. 5645-5650, 2002.
Bert U. W. Maes et al., "Synthesis of 4-aryl-5-hydroxy- and 5-aryl-4-hydroxypyridazin-3(2H)-ones and their use in the preparation of 4,5-diarylpyridazin-3(2H)-ones and hitherto unknown isochromeno[3,4-d]pyridazinediones", Tetrahedron, 58, pp. 9713-9721, 2002.
Edward C. Lawson et al., "Synthesis and Biological Evaluation of 1,2,4-Triazolo[2,3-a]pyrrole Derivatives as Alpha-4 ($a_4$) Integrin Antagonists", Letters in Drug Design & Discovery, 2, pp. 601-605, 2005.
Pal Tapolcsanyi et al., "Synthesis of the dibenzo[f,h]phthalazine and dibenzo[f,h]cinnoline skeleton via a 'Suzuki-Pd-catalyzed intramolecular arylation' and a 'Suzuki-Pschorr' approach", Tetrahedron, 59, pp. 5919-5926, 2003.
English abstract of Ukrainskii Khimicheskii Zhurnal (Russian Edition), 49(11), pp. 1197-1202, 1983.
English abstract of Dopovidi Akademii Nauk Ukrains'koi RSR, Seriya B: Geologichni, Khimichni ta Biologichni Nauki, (1), pp. 30-33, 1978.

(Continued)

*Primary Examiner* — Emily Bernhardt
(74) *Attorney, Agent, or Firm* — Wenderoth, Lind & Ponack, L.L.P.

(57) ABSTRACT

A pyridazinone compound represented by the formula (I)

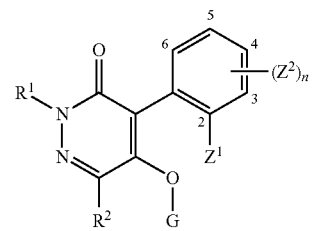

(I)

has excellent effect on weed control and is useful as an active ingredient of herbicides.

8 Claims, No Drawings

(56) References Cited

OTHER PUBLICATIONS

English abstract of CN 1676518 dated Oct. 5, 2005.
English abstract of CN 101041639 dated Sep. 26, 2007.
English abstract of CN 1962642 dated May 16, 2007.
Norbert Haider et al., "Thermolysis of 5-Azido-4-arylpyridazin-3(2H)-Ones: An Efficient and Versatile Synthesis of Pyridazino-4,5-b]indoles", Heterocycles, 68, pp. 2549-2561, 2006.
Su-Dong Cho et al., "Suzuki-Miyaura coupling reaction of aryl chlorides using di(2,6-dimethylmorpholino) phenylphosphine as ligand", Tetrahedron, 63, pp. 1345-1352, 2007.
Matthew D. Helm et al., "A novel approach to functionalised pyridazinone arrays", Organic & Biomolecular Chemistry, 4, pp. 4278-4280, 2006.
Yong Gong et al., "Synthesis and Biological Evaluation of Novel Pyridazinone-Based $\alpha_4$ Integrin Receptor Antagonists", J. Med. Chem., 49, pp. 3402-3411, 2006.
Office Action issued Jun. 1, 2012 in Colombian application No. 08074439, with English translation.
Canadian Office Action issued Mar. 25, 2013 in Canadian Application No. 2,645,272.
Office Action issued Sep. 17, 2014 in Indian Application No. 4933/CHENP/2008.

PYRIDAZINONE COMPOUND AND USE THEREOF

This application is a Divisional of U.S. application Ser. No. 13/426,894, filed Mar. 22, 2012, which is a Continuation of U.S. application Ser. No. 12/225,233, filed Sep. 17, 2008, now U.S. Pat. No. 8,541,414, which is a national stage application of International application No. PCT/JP2007/055579, filed Mar. 13, 2007.

TECHNICAL FIELD

The present invention relates to pyridazinone compounds and herbicides comprising thereof.

BACKGROUND ART

A certain type of pyridazinone compound is known in J. Heterocycl. Chem., vol. 42, pp. 427-435(2005).

However, said pyridazinone compound does not have enough weed controlling effect.

The subject of the present invention is to provide the compound with an excellent effect on weed control.

DISCLOSURE OF INVENTION

After extensive investigation, the present inventors discovered the pyridazinone compounds represented by the formula (I) have an excellent effect on weed control to complete the present invention.

The present invention is as the following.
(1) A pyridazinone compound represented by the formula (I) (hereinafter refer to the present compound),

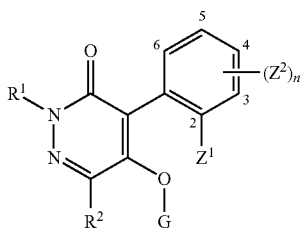

wherein in formula, $R^1$ represents a $C_{1-6}$ alkyl group or a ($C_{1-6}$ alkyloxy) $C_{1-6}$ alkyl group, $R^2$ represents a hydrogen atom or a $C_{1-6}$ alkyl group, G represents a hydrogen atom, a group represented by formula,

a group represented by formula,

or a group represented by formula,

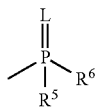

(wherein in formula, L represents an oxygen or a sulfur atom, $R^3$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkyloxy group, a $C_{3-8}$ cycloalkyloxy group, a $C_{2-6}$ alkenyloxy group, a $C_{2-6}$ alkynyloxy group, a $C_{6-10}$ aryloxy group, a ($C_{6-10}$ aryl) $C_{1-6}$ alkyloxy group, an amino group, a $C_{1-6}$ alkylamino group, a $C_{2-6}$ alkenylamino group, a $C_{6-10}$ arylamino group, di($C_{1-6}$ alkyl)amino group, di($C_{2-6}$ alkenyl)amino group, a ($C_{1-6}$ alkyl)($C_{6-10}$ aryl)amino group or a three- to eight-membered nitrogen containing heterocyclic ring group, $R^4$ represents a $C_{1-6}$ alkyl group, a $C_{6-10}$ aryl group, a $C_{1-6}$ alkylamino group or di($C_{1-6}$ alkyl)amino group and $R^5$ and $R^6$ may be same or different and represent a $C_{1-6}$ alkyl group, a $C_{3-8}$ cycloalkyl group, a $C_{2-6}$ alkenyl group, a $C_{6-10}$ aryl group, a $C_{1-6}$ alkyloxy group, a $C_{3-8}$ cycloalkyloxy group, a $C_{6-10}$ aryloxy group, a ($C_{6-10}$ aryl) $C_{1-6}$ alkyloxy group, a $C_{1-6}$ alkylthio group, $C_{1-6}$ alkylamino group or di($C_{1-6}$ alkyl)amino group, here, any group represented by $R^3$, $R^4$, $R^5$ and $R^6$ may be substituted with at least one halogen atom and a $C_{3-8}$ cycloalkyl group, a $C_{6-10}$ aryl group, an aryl moiety of a ($C_{6-10}$ aryl) $C_{1-6}$ alkyl group, a $C_{3-8}$ cycloalkyloxy group, a $C_{6-10}$ aryloxy group, an aryl moiety of a ($C_{6-10}$ aryl) $C_{1-6}$ alkyloxy group, an aryl moiety of a $C_{6-10}$ arylamino group, an aryl moiety of a ($C_{1-6}$ alkyl) ($C_{6-10}$ aryl)amino group and a three- to eight-membered nitrogen containing heterocyclic ring group may be substituted with at least one $C_{1-6}$ alkyl group), $Z^1$ represents a $C_{1-6}$ alkyl group, $Z^2$ represents a $C_{1-6}$ alkyl group, n represents 0, 1, 2, 3 or 4 and each of $Z^2$ may be same or different when n represents an integer of 2 or more, and a sum of the number of carbon atoms in the group represented by $Z^1$ and that in the group represented by $Z^2$ is equal to 2 or more.

(2) The pyridazinone compound according to (1), wherein n is an integer equal to 1 or more.

(3) The pyridazinone compound according to (1), wherein n is 0 and $Z^1$ is a $C_{2-6}$ alkyl group.

(4) The pyridazinone compound according to (1), wherein n is 1 or 2 and $Z^2$ is (a) substituent(s) on 4- and/or 6-position of a benzene ring.

(5) The pyridazinone compound according to (1), (2) or (4), wherein $Z^1$ is a $C_{1-3}$ alkyl group and $Z^2$ is a $C_{1-3}$ alkyl group.

(6) The pyridazinone compound according to any one of (1) to (5), wherein G represents a hydrogen atom, a group represented by formula,

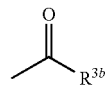

a group represented by formula

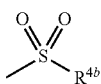

or a group represented by formula,

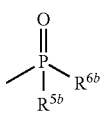

wherein in formula, $R^{3b}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkyloxy group, a $C_{3-8}$ cycloalkyloxy group, a $C_{6-10}$ aryloxy group, a ($C_{6-10}$ aryl) $C_{1-6}$ alkyloxy group, a $C_{1-6}$ alkylamino group, a $C_{6-10}$ arylamino group or di($C_{1-6}$ alkyl)amino group, $R^{4b}$ represents a $C_{1-6}$ alkyl group or a $C_{6-10}$ aryl group and $R^{5b}$ and $R^{6b}$ may be same or different and represent a $C_{1-6}$ alkyl group, a $C_{1-6}$ alkyloxy group, a $C_{6-10}$ aryloxy group or a $C_{1-6}$ alkylthio group, here, any group represented by $R^{3b}$, $R^{4b}$, $R^{5b}$ and $R^{6b}$ may be substituted with at least one halogen atom and a $C_{3-8}$ cycloalkyl group, a $C_{6-10}$ aryl group, an aryl moiety of a ($C_{6-10}$ aryl) $C_{1-6}$ alkyl group, a $C_{3-8}$ cycloalkyloxy group, a $C_{6-10}$ aryloxy group, an aryl moiety of a ($C_{6-10}$ aryl) $C_{1-6}$ alkyloxy group and an aryl moiety of a $C_{6-10}$ arylamino group may be substituted with at least one $C_{1-6}$ alkyl group.

(7) The pyridazinone compound according to any one of (1) to (5), wherein G represents a hydrogen atom, a group represented by formula,

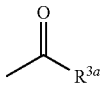

or a group represented by formula,

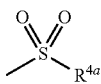

wherein in formula, $R^{3a}$ represents a $C_{1-6}$ alkyl group, a $C_{3-8}$ cycloalkyl group, a $C_{6-10}$ aryl group, a $C_{1-6}$ alkyloxy group or di($C_{1-6}$ alkyl) amino group and $R^{4a}$ represents a $C_{1-6}$ alkyl group, here, any group represented by $R^{3a}$ and $R^{4a}$ may be substituted with at least one halogen atom and a $C_{3-8}$ cycloalkyl group and a $C_{6-10}$ aryl group may be substituted with at least one $C_{1-6}$ alkyl group.

(8) The pyridazinone compound according to any one of (1) to (7), wherein $R^2$ is a hydrogen atom or a $C_{1-3}$ alkyl group.

(9) The pyridazinone compound according to any one of (1) to (7), wherein $R^2$ is a hydrogen atom or a methyl group.

(10) The pyridazinone compound according to any one of (1) to (9), wherein $R^1$ is a $C_{1-3}$ alkyl group or a ($C_{1-3}$ alkyloxy) $C_{1-3}$ alkyl group.

(11) A herbicide comprising the pyridazinone compound according to any one of (1) to (10) as an active ingredient.

(12) A weed controlling method comprising a step, in which an effective amount of the pyridazinone compound according to any one of (1) to (10) is applied to weeds or soil where weeds are grown.

(13) Use of the pyridazinone compound according to any one of (1) to (10) for weed control.

(14) A compound represented by the formula (II):

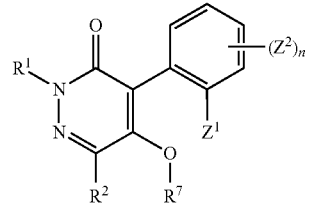

wherein in formula, $R^7$ represents a $C_{1-6}$ alkyl group, $R^1$, $R^2$, $Z^1$, $Z^2$ and n have the same meaning as defined in (1).

(15) A compound represented by the formula (VI):

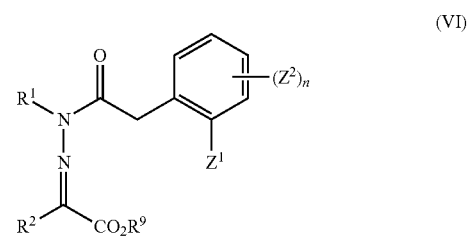

wherein in formula, $R^9$ represents a $C_{1-6}$ alkyl group, $R^1$, $R^2$, $Z^1$, $Z^2$ and n have the same meaning as defined in (1).

In substituents represented by $R^1$, $R^2$, $R^3$, $R^4$, $R^5$, $R^6$, $Z^1$, and $Z^2$ in the formula (I) of the present invention, a $C_{1-6}$ alkyl group denotes an alkyl group with the number of carbon atoms from 1 to 6 and includes, for example, a methyl group, an ethyl group, a propyl group, an isopropyl group, a butyl group, an isobutyl group, a sec-butyl group, a tert-butyl group, a pentyl group, a sec-pentyl group, an isopentyl group, a neopentyl group, a hexyl group, an isohexyl group, etc., a $C_{3-8}$ cycloalkyl group denotes a cycloalkyl group with the number of carbon atoms from 3 to 8 and includes, for example, a cyclopropyl group, a cyclopentyl group, a cyclohexyl group, etc., a $C_{2-6}$ alkenyl group denotes an alkenyl group with the number of carbon atoms from 2 to 6 and includes, for example, an allyl group, a 1-buten-3-yl group, a 3-buten-1-yl group, etc., a $C_{2-6}$ alkynyl group denotes an alkynyl group with the number of carbon atoms from 2 to 6 and includes, for example, a propargyl group, 2-butynyl group, etc., a $C_{6-10}$ aryl group denotes an aryl group with the number of carbon atoms from 6 to 10 and includes, for example, a phenyl group, a naphthyl group, etc., a ($C_{6-10}$ aryl) $C_{1-6}$ alkyl group denotes a $C_{1-6}$ alkyl group substituted with a $C_{6-10}$ aryl group and includes, for example, a benzyl group, a phenethyl group, etc., a $C_{1-6}$ alkyloxy group denotes an alkyloxy group with the number of carbon atoms from 1 to 6 and includes, for example, a methoxy group, an ethoxy group, a propoxy group, an isopropoxy group, etc., a $C_{3-8}$ cycloalkyloxy group denotes a cycloalkyloxy group with the number of carbon atoms from 3 to 8 and includes, for example, a cyclopropyloxy group, a cyclopentyloxy group, etc., a $C_{2-6}$ alkenyloxy group denotes an alkenyloxy group with the number of carbon atoms from 2 to 6 and includes, for example, a vinyloxy group, an allyloxy group, etc., a $C_{2-6}$ alkynyloxy group denotes an alkynyloxy group with the number of carbon atoms from 2 to 6 and includes, for example, a propargyloxy group, 2-butynyloxy group, etc., a $C_{6-10}$ aryloxy group denotes an aryloxy group with the number of carbon atoms from 6 to 10 and includes, for example, a phenoxy group, a naphthoxy group, etc., a ($C_{6-10}$ aryl) $C_{1-6}$ alkyloxy group denotes a $C_{1-6}$ alkyloxy group substituted with a $C_{6-10}$ aryl group and includes, for example, a benzyloxy group, a phenethyloxy group, etc., a $C_{1-6}$ alkylamino group denotes an alkylamino group with the number of carbon atoms from 1 to 6 and includes, for example, a methylamino group, an ethylamino group, etc., a $C_{2-6}$ alkenylamino group denotes an alkenylamino group with the number of carbon atoms from 2 to 6 and includes, for example, an allylamino group, a 3-butenylamino group, etc., member atom(s) and includes, for example, a 1-pyrazolyl group, a 2-pyridyl group, a 2-pyrimidinyl group, a 2-thiazolyl group, a pyrrolidino group, a piperidino group, a morpholino group, etc.

The group represented by $R^3$, $R^4$, $R^5$ and $R^6$ may be substituted with at least one halogen atom and such halogen atom includes, for example, a fluorine atom, a chlorine atom, a bromine atom or an iodine atom.

In the group represented by $R^3$, $R^4$, $R^5$ and $R^6$, a $C_{3-8}$ cycloalkyl group, a $C_{6-10}$ aryl group, an aryl moiety of a ($C_{6-10}$ aryl) $C_{1-6}$ alkyl group, a $C_{3-8}$ cycloalkyloxy group, a $C_{6-10}$ aryloxy group, an aryl moiety of a ($C_{6-10}$ aryl) $C_{1-6}$ alkyloxy group, an aryl moiety of a $C_{6-10}$ arylamino group, an aryl moiety of a ($C_{1-6}$ alkyl) ($C_{6-10}$ aryl)amino group and a three- to eight-membered nitrogen containing heterocyclic ring group may be substituted with a $C_{1-6}$ alkyl group and such a $C_{1-6}$ alkyl group includes, for example, a methyl group, an ethyl group, a propyl group, a butyl group and the like.

Among the present compound, the compound represented by the formula (I-a), of which G is a hydrogen atom may take place in a form of tautomers represented by the formulas (I-a') and (I-a"). The compound represented by the formula (I-a) includes all of such tautomers and a mixture of any two or more of them.

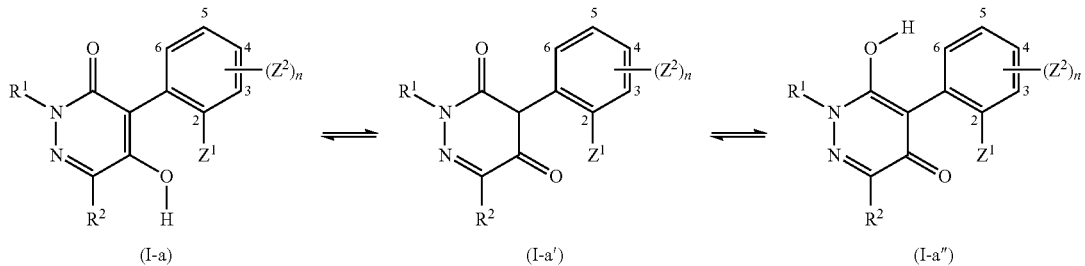

a $C_{6-10}$ arylamino group denotes an arylamino group with the number of carbon atoms from 6 to 10 and includes, for example, a phenylamino group, a naphthylamino group, etc., a di($C_{1-6}$ alkylamino group denotes an amino group substituted with two same or different $C_{1-6}$ alkyl groups and includes, for example, a dimethylamino group, a diethylamino group, an N-ethyl-N-methylamino group, etc., a di($C_{2-6}$ alkenyl)amino group denotes an amino group substituted with two same or different $C_{2-6}$ alkenyl groups and includes, for example, a diallylamino group, a di(3-butenyl)amino group, etc., a ($C_{1-6}$ alkyl) ($C_{6-10}$ aryl)amino group denotes an amino group substituted with a $C_{1-6}$ alkyl group and a $C_{6-10}$ aryl group and includes, for example, a methylphenylamino group, an ethylphenylamino group, etc., a $C_{1-6}$ alkylthio group denotes an alkylthio group with the number of carbon atoms from 1 to 6 and includes, for example, a methylthio group, an ethylthio group, a propylthio group, an isopropylthio group, etc., a ($C_{1-6}$ alkyloxy) $C_{1-6}$ alkyl group denotes a $C_{1-6}$ alkyl group substituted with a $C_{1-6}$ alkyloxy group and includes, for example, a methoxyethyl group, an ethoxyethyl group, etc., and a three- to eight-membered nitrogen containing heterocyclic ring group denotes an aromatic or alicyclic three- to eight-membered heterocyclic ring group comprising one to three nitrogen atoms as a ring member atom(s) and optionally comprising one to three oxygen and/or sulfur atom(s) as a ring The salt of the compound represented by the formula (I-a) can be also obtained, for example, by mixing the compound represented by the formula (I-a) with an inorganic base (for example, hydroxide, carbonate, hydrogen carbonate, acetate, hydride or others of an alkali metal (lithium, sodium, potassium, etc.); hydroxide, hydride or others of an alkali earth metal (magnesium, calcium, barium, etc.) or ammonia); an organic base (for example, dimethylamine, triethylamine, piperazine, pyrrolidine, piperidine, 2-phenylethylamine, benzylamine, ethanolamine, diethanolamine, pyridine, collidine, etc.) or a metal alkoxide (for example, sodium methoxide, potassium tert-butoxide, magnesium methoxide, etc.). The present invention includes agriculturally acceptable salts of the compounds represented by formula (I-a).

When the present compound has one or more asymmetric centers, the present compound takes place in a form of two or more stereoisomers (for example, enantiomers, diastereomers or the like). The present compound includes all of such stereoisomers and a mixture of any two or more of them.

When the present compound has geometric isomerism based on a double bond or the like, said compound also takes place in a form of two or more geometric isomers (for example, each isomer of E/Z- or trans/cis-isomers, each isomer of S-trans/S-cis-isomers or others). The present compound includes all of such geometric isomers and a mixture of any two or more of them.

Preferred embodiments of the present compounds include, for example, the following embodiment among the present compounds.

The pyridazinone compound in the formula (I), wherein n is an integer of 1 or more.

The pyridazinone compound in the formula (I), wherein n is 0 and $Z^1$ is a $C_{2-6}$ alkyl group.

The pyridazinone compound in the formula (I), wherein n is 1 or 2 and $Z^2$ is bonded at a 4- and/or 6-position of the benzene ring.

The pyridazinone compound in the formula (I), wherein G is a hydrogen atom, a group represented by formula,

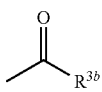

a group represented by formula,

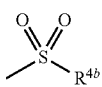

or a group represented by formula,

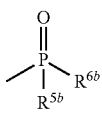

(wherein in formula, $R^{3b}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a ($C_{6-10}$ aryl) $C_{1-6}$ alkyl group, a $C_{1-6}$ alkyloxy group, a $C_{3-8}$ cycloalkyloxy group, a $C_{6-10}$ aryloxy group, a ($C_{6-10}$ aryl) $C_{1-6}$ alkyloxy group, a $C_{1-6}$ alkylamino group, a $C_{6-10}$ arylamino group or di($C_{1-6}$ alkyl)amino group, $R^{4b}$ represents a $C_{1-6}$ alkyl group or a $C_{6-10}$ aryl group and $R^{5b}$ and $R^{6b}$ may be same or different and represent a $C_{1-6}$ alkyl group, a $C_{1-6}$ alkyloxy group, a $C_{6-10}$ aryloxy group or a $C_{1-6}$ alkylthio group, here, any group represented by $R^{3b}$, $R^{4b}$, $R^{5b}$ and $R^{6b}$ may be substituted with at least one halogen atom and a $C_{3-8}$ cycloalkyl group, a $C_{6-10}$ aryl group, an aryl moiety of a ($C_{6-10}$ aryl) $C_{1-6}$ alkyl group, a $C_{3-8}$ cycloalkyloxy group, a $C_{6-10}$ aryloxy group, an aryl moiety of a ($C_{6-10}$ aryl) $C_{1-6}$ alkyloxy group and an aryl moiety of a $C_{6-10}$ arylamino group may be substituted with at least one $C_{1-6}$ alkyl group.)

The pyridazinone compound in the formula (I), wherein G is a hydrogen atom, a group represented by formula,

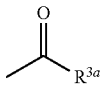

or a group represented by formula,

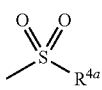

(wherein in formula, $R^{3a}$ represents a $C_{1-6}$ alkyl group, a $C_{3-8}$ cycloalkyl group, a $C_{6-10}$ aryl group, a $C_{1-6}$ alkyloxy group or a di($C_{1-6}$ alkyl) amino group and $R^{4a}$ represents a $C_{1-6}$ alkyl group, here, any group represented by $R^{3a}$ and $R^{4a}$ may be substituted with at least one halogen atom and a $C_{3-8}$ cycloalkyl group and a $C_{6-10}$ aryl group may be substituted with at least one $C_{1-6}$ alkyl group.)

The pyridazinone compound in the formula (I), wherein $R^1$ is a $C_{1-3}$ alkyl group or a ($C_{1-3}$ alkyloxy) $C_{1-3}$ alkyl group.

The pyridazinone compound in the formula (I), wherein $R^2$ is a hydrogen atom or a $C_{1-3}$ alkyl group.

The pyridazinone compound in the formula (I), wherein $R^2$ is a hydrogen atom or a methyl group.

The pyridazinone compound in the formula (I), wherein $Z^1$ is a $C_{1-3}$ alkyl group and $Z^2$ is a $C_{1-3}$ alkyl group.

The pyridazinone compound in the formula (I), wherein $R^1$ is a $C_{1-3}$ alkyl group or a ($C_{1-3}$ alkyloxy) $C_{1-3}$ alkyl group and $R^2$ is a hydrogen atom or a $C_{1-3}$ alkyl group.

The pyridazinone compound in the formula (I), wherein $R^1$ is a $C_{1-3}$ alkyl group or a ($C_{1-3}$ alkyloxy) $C_{1-3}$ alkyl group and $R^2$ is a hydrogen atom or a methyl group.

The pyridazinone compound in the formula (I), wherein $R^2$ is a hydrogen atom or a $C_{1-3}$ alkyl group and G is a hydrogen atom, a group represented by formula,

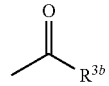

a group represented by formula,

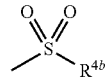

or a group represented by formula,

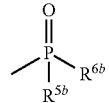

(wherein in formula, $R^{3b}$, $R^{4b}$, $R^{5b}$ and $R^{6b}$ denote the same as the above mentioned).

The pyridazinone compound in the formula (I), wherein $R^2$ is a hydrogen atom or a $C_{1-3}$ alkyl group and G is a hydrogen atom, a group represented by formula,

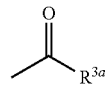

or a group represented by formula,

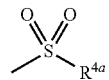

(wherein in formula, $R^{3a}$ and $R^{4a}$ denote the same as the above mentioned).

The pyridazinone compound in the formula (I), wherein $R^2$ is a hydrogen atom or a methyl group, G is a hydrogen atom, a group represented by formula,

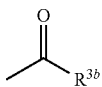

a group represented by formula,

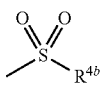

or a group represented by formula,

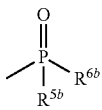

(wherein in formula, $R^{3b}$, $R^{4b}$, $R^{5b}$ and $R^{6b}$ denote the same as the above mentioned).

The pyridazinone compound in the formula (I), wherein $R^2$ is a hydrogen atom or a methyl group and G is a hydrogen atom, a group represented by formula,

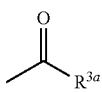

or a group represented by formula,

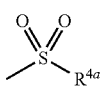

(wherein in formula, $R^{3a}$ and $R^{4a}$ denote the same as the above mentioned).

The pyridazinone compound in the formula (I), wherein $R^1$ is a $C_{1-3}$ alkyl group or a ($C_{1-3}$ alkyloxy) $C_{1-3}$ alkyl group, $R^2$ is a hydrogen atom or a $C_{1-3}$ alkyl group and G is a hydrogen atom, a group represented by formula,

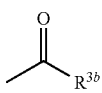

a group represented by formula,

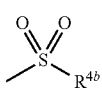

or a group represented by formula,

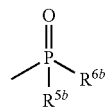

(wherein in formula, $R^{3b}$, $R^{4b}$, $R^{5b}$ and $R^{6b}$ denote the same as the above mentioned).

The pyridazinone compound in the formula (I), wherein $R^1$ is a $C_{1-3}$ alkyl group or a ($C_{1-3}$ alkyloxy) $C_{1-3}$ alkyl group and $R^2$ is a hydrogen atom or a $C_{1-3}$ alkyl group and G is a hydrogen atom, a group represented by formula,

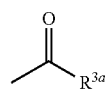

or a group represented by formula,

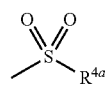

(wherein in formula, $R^{3a}$ and $R^{4a}$ denote the same as the above mentioned).

The pyridazinone compound in the formula (I), wherein $R^1$ is a $C_{1-3}$ alkyl group or a ($C_{1-3}$ alkyloxy) $C_{1-3}$ alkyl group, $R^2$ is a hydrogen atom or a methyl group and G is a hydrogen atom, a group represented by formula,

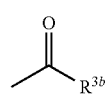

a group represented by formula,

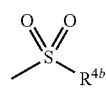

or a group represented by formula,

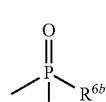

(wherein in formula, $R^{3b}$, $R^{4b}$, $R^{5b}$ and $R^{6b}$ denote the same as the above mentioned).

The pyridazinone compound in the formula (I), wherein $R^1$ is a $C_{1-3}$ alkyl group or a ($C_{1-3}$ alkyloxy) $C_{1-3}$ alkyl group, $R^2$ is a hydrogen atom or a methyl group and G is a hydrogen atom, a group represented by formula, $$\underset{R^{3a}}{\overset{O}{\|}}$$

or a group represented by formula, $$\underset{R^{4a}}{\overset{O\diagdown\diagup O}{S}}$$

(wherein in formula, $R^{3a}$ and $R^{4a}$ denote the same as the above mentioned.)

The pyridazinone compound in the formula (I), wherein $R^1$ is a $C_{1-3}$ alkyl group or a $(C_{1-3}$ alkyloxy$) C_{1-3}$ alkyl group, $R^2$ is a hydrogen atom or $C_{1-3}$ alkyl group, n represents 0, 1 or 2 and each of $Z^2$ may be same or different when n represents 2, and when n represents 1 or 2, $Z^2$ is (a) substituent(s) on 4- and/or 6-position of a benzene ring, $Z^1$ is a $C_{1-6}$ alkyl group (preferably a $C_{1-3}$ alkyl group) and $Z^2$ is a $C_{1-6}$ alkyl group (preferably a $C_{1-3}$ alkyl group).

The pyridazinone compound in the formula (I), wherein $R^1$ is a $C_{1-3}$ alkyl group or a $(C_{1-3}$ alkyloxy$) C_{1-3}$ alkyl group, $R^2$ is a hydrogen atom or $C_{1-3}$ alkyl group and G is a hydrogen atom, a group represented by formula, $$\underset{R^{3b}}{\overset{O}{\|}}$$

a group represented by formula, $$\underset{R^{4b}}{\overset{O\diagdown\diagup O}{S}}$$

or a group represented by formula, $$\underset{\underset{R^{5b}}{|}}{\overset{\overset{O}{\|}}{P}}\!-\!R^{6b}$$

(wherein in formula, $R^{3b}$, $R^{4b}$, $R^{5b}$ and $R^{6b}$ denote the same as the above mentioned), n represents 0, 1 or 2 and each of $Z^2$ may be same or different when n represents 2, and when n represents 1 or 2, $Z^2$ is (a) substituent(s) on 4- and/or 6-position of a benzene ring, $Z^1$ is a $C_{1-6}$ alkyl group (preferably a $C_{1-3}$ alkyl group) and $Z^2$ is a $C_{1-6}$ alkyl group (preferably a $C_{1-3}$ alkyl group).

The pyridazinone compound in the formula (I), wherein $R^1$ is a $C_{1-3}$ alkyl group or a $(C_{1-3}$ alkyloxy$) C_{1-3}$ alkyl group, $R^2$ is a hydrogen atom or a $C_{1-3}$ alkyl group, G is a hydrogen atom, a group represented by formula, $$\underset{R^{3a}}{\overset{O}{\|}}$$

or a group represented by formula, $$\underset{R^{4a}}{\overset{O\diagdown\diagup O}{S}}$$

(wherein in formula, $R^{3a}$ and $R^{4a}$ denote the same as the above mentioned), n represents 0, 1 or 2 and each of $Z^2$ may be same or different when n represents 2, and when n represents 1 or 2, $Z^2$ is (a) substituent(s) on 4- and/or 6-position of a benzene ring, $Z^1$ is a $C_{1-6}$ alkyl group (preferably a $C_{1-3}$ alkyl group) and $Z^2$ is a $C_{1-6}$ alkyl group (preferably a $C_{1-3}$ alkyl group).

The pyridazinone compound in the formula (I), wherein $R^1$ is a $C_{1-3}$ alkyl group or a $(C_{1-3}$ alkyloxy$) C_{1-3}$ alkyl group, $R^2$ is a hydrogen atom or a methyl group, n represents 0, 1 or 2 and each of $Z^2$ may be same or different when n represents 2, and when n represents 1 or 2, $Z^2$ is (a) substituent(s) on 4- and/or 6-position of a benzene ring, $Z^1$ is a $C_{1-6}$ alkyl group (preferably a $C_{1-3}$ alkyl group) and $Z^2$ is a $C_{1-6}$ alkyl group (preferably a $C_{1-3}$ alkyl group).

The pyridazinone compound in the formula (I), wherein $R^1$ is a $C_{1-3}$ alkyl group or a $(C_{1-3}$ alkyloxy$) C_{1-3}$ alkyl group, $R^2$ is a hydrogen atom or a methyl group, G is a hydrogen atom, a group represented by formula, $$\underset{R^{3b}}{\overset{O}{\|}}$$

a group represented by formula, $$\underset{R^{4b}}{\overset{O\diagdown\diagup O}{S}}$$

or a group represented by formula, $$\underset{\underset{R^{5b}}{|}}{\overset{\overset{O}{\|}}{P}}\!-\!R^{6b}$$

(wherein in formula, $R^{3b}$, $R^{4b}$, $R^{5b}$ and $R^{6b}$ denote the same as the above mentioned), n represents 0, 1 or 2 and each of $Z^2$ may be same or different when n represents 2, and when n represents 1 or 2, $Z^2$ is (a) substituent(s) on 4- and/or 6-position of a benzene ring, $Z^1$ is a $C_{1-6}$ alkyl group (preferably a $C_{1-3}$ alkyl group) and $Z^2$ is a $C_{1-6}$ alkyl group (preferably a $C_{1-3}$ alkyl group).

The pyridazinone compound in the formula (I), wherein $R^1$ is a $C_{1-3}$ alkyl group or a $(C_{1-3}$ alkyloxy$) C_{1-3}$ alkyl group, $R^2$ is a hydrogen atom or a methyl group, G is a hydrogen atom, a group represented by formula,

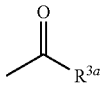

or a group represented by formula,

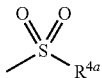

(wherein in formula, $R^{3a}$ and $R^{4a}$ denote the same as the above mentioned), n represents 0, 1 or 2 and each of $Z^2$ may be same or different when n represents 2, and when n represents 1 or 2, $Z^2$ is (a) substituent(s) on 4- and/or 6-position of a benzene ring, $Z^1$ is a $C_{1-6}$ alkyl group (preferably a $C_{1-3}$ alkyl group) and $Z^2$ is a $C_{1-6}$ alkyl group (preferably a $C_{1-3}$ alkyl group).

The pyridazinone compound represented by the formula (I-1),

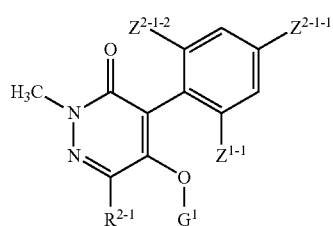

(wherein in formula, $R^{2-1}$ represents a hydrogen atom or a $C_{1-3}$ alkyl group, $G^1$ represents a hydrogen atom, a $C_{1-3}$ alkylcarbonyl group optionally substituted by at least one halogen atom, a $C_{1-3}$ alkoxycarbonyl group or a $C_{6-10}$ arylcarbonyl group, $Z^{1-1}$ represents a alkyl group, $Z^{2-1-1}$ represents a $C_{1-3}$ alkyl group and $Z^{2-1-2}$ represents a hydrogen atom or a $C_{1-3}$ alkyl group).

The pyridazinone compound in the formula (I-1), wherein $R^{2-1}$ is a hydrogen atom, a methyl group or an ethyl group, $G^1$ is a hydrogen atom, an acetyl group, a propionyl group, a methoxycarbonyl group, an ethoxycarbonyl group or a benzoyl group, $Z^{1-1}$ is a methyl group or an ethyl group, $Z^{2-1-1}$ is a methyl group or an ethyl group and $Z^{2-1-2}$ is a hydrogen atom, a methyl group or an ethyl group).

The pyridazinone compound represented by the formula (I-2)

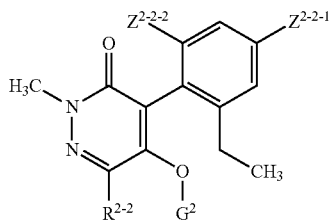

(wherein in formula, $R^{2-2}$ represents a hydrogen atom or a $C_{1-3}$ alkyl group, $G^2$ represents a hydrogen atom, a $C_{1-3}$ alkylcarbonyl group optionally substituted by at least one halogen atom or a $C_{1-3}$ alkoxycarbonyl group, $Z^{2-2-1}$ represents a hydrogen atom or a $C_{1-3}$ alkyl group and $Z^{2-2-2}$ represents a hydrogen atom or a $C_{1-3}$ alkyl group).

The pyridazinone compound in the formula (I-2), wherein $R^{2-2}$ is a hydrogen atom, a methyl group or an ethyl group, $G^2$ is a hydrogen atom, an acetyl group, a methoxycarbonyl group or an ethoxycarbonyl group $Z^{2-2-1}$ is a hydrogen atom, a methyl group or an ethyl group and $Z^{2-2-2}$ is a hydrogen atom, a methyl group or an ethyl group).

The present compounds have an excellent weed controlling activity and can be used as an active ingredient of herbicide. Some of the present compounds have selectivity between crops and weeds. Examples of the weeds which the present compounds can control include following:

Weeds in fields such as *Digitaria adscendens, Eleusine indica, Setaria viridis, Setaria faberi, Setaria glauca, Echinochloa crus-galli, Panicum dichotomiflorum, Brachiaria platyphylla, Sorghum halepense, Sorghum bicolor, Cynodon dactylon, Avena fatua, Lolium multiflorum, Alopecurus myosuroides, Bromus tectorum, Bromus sterilis, Phalaris minor, Aperaspica-venti, Poa annua, Agropyron repens, Cyperus rotundus, Cyperus esculentus, Amaranthus retroflexus, Portulaca oleracea, Abutilon theophrasti, Chenopodium album, Polygonum longisetum, Solanum nigrum, Sida spinosa, Datura stramonium, Ipomoea purpurea, Xanthium strumarium, Cassia obtusifolia, Ambrosia artemisiifolia, Commelina communis, Galium aparine, Stellaria media, Brassica* spp., *Matricaria chamomilla, Veronica persica, Viola arvensis, Papaver rhoeas, Convolvulus arvensis, Erigeron canadensis* and the like;

weeds in paddy fields such as *Echinochloa oryzicola, Echinochloa crus-galli, Cyperus difformis, Cyperus iria, Fimbristylis miliacea, Eleocharis acicularis, Scirpus juncoides, Scirpus wallichii, Cyperus serotinas, Eleocharis kuroguwai, Scirpus planiculmis, Scirpus nipponicus, Monochoria vaginalis, Lindernia procumbens, Dopatrium junceum, Rotala indica, Ammannia multiflora, Elatine triandra, Ludwigia prostrata, Sagittaria pygmaea, Alisma canaliculatum, Sagittaria trifolia, Potamogeton distinctus, Oenanthe javanica, Callitriche verna, Vandellia angustifolia, Lindernia dubia, Eclipta prostrata, Murdannia keisak, Paspalum distichum, Leersia oryzoides* and the like.

The present compound can be used for a herbicide of agricultural field such as field, paddy field, lawn, orchard and the like and non-agricultural field. Especially, it is suitable for herbicide in field. In some cases, weeds can be controlled without damage to crops by using the present compound in agricultural field where crops such as wheat, barley, soy bean, corn, cotton, rice and the like is growing.

When the present compound is used as an active ingredient of herbicides, the present compound are generally formulated in a dosage form suitable for a purpose of use by dissolving or dispersing in a proper liquid carrier or mixing with or absorbing to a proper solid carrier. Herbicides comprising the present compound are a formulated product, for example, in a form of emulsifiable concentrate, soluble concentrate, oil solution, aerosol, wettable powder, dust, less drifting dust, granule, micro granule, micro granule F, fine granule F, water dispersible granule, water soluble powder, flowable, dry flowable, jumbo tablet which means bagged self-diffusible powder, tablets, pastes or others. Such formulation can be further prepared as needed by adding auxiliary agents, for instance, emulsifiers, dispersants, spreading agents, penetrating agents, wetting agents, binders, thickeners, preservatives, antioxidants, colorants or others according to a known method.

The liquid carrier used in formulation includes, for example, water, alcohols (for example, methanol, ethanol, 1-propanol, 2-propanol, ethylene glycol, etc.), ketones (for example, acetone, methyl ethyl ketone, etc.), ethers (for example, dioxane, tetrahydrofuran, ethylene glycol monomethyl ether, diethylene glycol monomethyl ether, propylene glycol monomethyl ether, etc.), aliphatic hydrocarbons (for example, hexane, octane, cyclohexane, kerosene, burning oil, machine oil, etc.), aromatic hydrocarbons (for example, benzene, toluene, xylene, solvent naphtha, methylnaphthalene, etc.), halogenated hydrocarbons (for example, dichloromethane, chloroform, carbontetrachloride, etc.), acid amides (for example, dimethylformamide, dimethylacetamide, N-methylpyrrolidone, etc.), esters (for example, ethyl acetate, butyl acetate, glyceryl fatty acid ester, etc.), nitriles (for example, acetonitrile, propionitrile, etc.) and the like. Two or more of such liquid carriers may be mixed in a proper ratio for use.

The solid carrier used in formulation includes plant powder (for example, soy flour, alfalfa flour, wheat flour, wood flour, etc.), mineral powder (for example, clays such as kaolin, bentonite, acid clay, clay, etc., talcs such as talc powder, pyrophillite powder, etc., silica such as diatomaceous earth, mica powder, etc.), alumina, sulfur powder, active charcoal, saccharides (for example, lactose, glucose, etc.), inorganic salts (for example, calcium carbonate, sodium bicarbonate, etc.), glass hollow bodies (natural vitreous materials being calcined to encapsulate air bubbles in it) and the like. Two or more of such solid carriers may be mixed in a proper ratio for use.

The amount of the liquid carrier or solid carrier used is generally 1 to 99% by weight, preferably about 10 to 99% by weight against total amount of the formulation.

Surfactants are generally used as emulsifiers, dispersants, spreading agents, penetrating agents, wetting agents or others used in formulation. Surfactants include, for example, anionic surfactants such as alkyl sulfate ester salts, alkylarylsulfonates, dialkyl sulfosuccinates, polyoxyethylene alkylaryl ether phosphate salts, lignin sulfonate, naphthalenesulfonate-formaldehyde polycondensates, etc., and nonionic surfactants such as polyoxyethylene alkyl ether, polyoxyethylene alkylaryl ether, polyoxyethylenealkyl polyoxypropylene block copolymer, sorbitol fatty acid ester and the like. Two or more of such surfactants may be used. The amount of the surfactant used is generally 0.1 to 50% by weight, preferably about 0.1 to 25% by weight against a total amount of the formulation.

Binders and thickeners include, for example, dextrin, sodium salt of carboxylmethylcellulose, polycarboxylic acid type polymers, polyvinylpyrrolidone, polyvinyl alcohol, sodium lignin sulfonate, calcium lignin sulfonate, sodium polyacrylate, gum acacia, sodium alginate, mannitol, sorbitol, bentonite type mineral matters, polyacrylic acid and derivatives thereof, white carbon, natural saccharide derivatives (for example, xanthan gum, guar gum, etc.) or others.

The content ratio of the present compound in the formulation is generally 1 to 90% by weight in the form of the emulsifiable concentrate, wettable powder, water dispersible granule, soluble concentrate, water soluble powder, flowable and the like, generally 0.01 to 10% by weight in the form of the oil miscible liquid, dust, less drifting dust and the like and generally 0.05 to 10% by weight in the form of the micro granule, micro granule F, fine granule F, granule and the like, respectively, but the concentration may appropriately be varied according to a purpose of use. The emulsifiable concentrate, wettable powder, water dispersible granule, soluble concentrate, water soluble powder, flowable or others are generally properly diluted with water or others and generally used after diluting to about 100 to 100,000 times the concentration of the ingredient.

The method to apply the herbicides comprising the present compound as an active ingredient is similar to a conventional general application method for known agricultural chemicals and includes, for example, aerial spraying, soil broadcast, foliage application or the like.

When the herbicides comprising the present compound as an active ingredient is used as the herbicide for dry or paddy field, the amount thereof may be varied with an applied area, an applied time of year, an application method, target weed species, cultivated crop or the like, but generally in the range of 1 to 5000 g, preferably in the range of 10 to 1000 g of the present compound per one hectare of dry or paddy field.

The herbicides comprising the present compound as an active ingredient for weed control in the dry field are generally used as a pre-emergence soil incorporation treatment agent, pre-emergence soil treatment agent or post-emergence foliage treatment agent. Such herbicides for weed control in the paddy field is generally used as a pre-emergence soil treatment agent or both foliage and soil treatment agent.

The herbicide which comprises the present compound as an active ingredient can simultaneously be applied, if necessary, with one or more kinds of other herbicides, plant growth regulators, fungicides, insecticides, acaricides, nematocides and the like. Or it can be used in combination with one or more kinds of other herbicides, plant growth regulators, fungicides, insecticides, acaricides, nematocides and the like.

Active ingredients of the other herbicide which can simultaneously be applied and/or can be used in combination with the present compound include, for example, as follows:

(1) herbicidal phenoxyfatty acid compounds [2,4-PA, MCP, MCPB, phenothiol, mecoprop, fluroxypyr, triclopyr, clomeprop, naproanilide and the like], (2) herbicidal benzoic acid compounds [2,3,6-TBA, dicamba, clopyralid, picloram, aminopyralid, quinclorac, quinmerac and the like], (3) herbicidal urea compounds [diuron, linuron, chlortoluron, isoproturon, fluometuron, isouron, tebuthiuron, methabenzthiazuron, cumyluron, daimuron, methyl-daimuron and the like], (4) herbicidal triazinecompounds [atrazine, ametoryn, cyanazine, simazine, propazine, simetryn, dimethametryn, prometryn, metribuzin, triaziflam and the like], (5) herbicidal bipyridinium compounds [paraquat, diquat and the like], (6) herbicidal hydroxybenzonitrile compounds [bromoxynil, ioxynil and the like], (7) herbicidal dinitroaniline compounds [pendimethalin, prodiamine, trifluralin and the like],
(8) herbicidal organophosphorus compounds [amiprofos-methyl, butamifos, bensulide, piperophos, anilofos, glyphosate, glufosinate, bialaphos and the like],
(9) herbicidal carbamate compounds [di-allate, tri-allate, EPTC, butylate, benthiocarb, esprocarb, molinate, dimepiperate, swep, chlorpropham, phenmedipham, phenisopham, pyributicarb, asulam and the like],
(10) herbicidal acid amide compounds [propanil, propyzamide, bromobutide, etobenzanid and the like],
(11) herbicidal chloroacetoanilide compounds [acetochlor, alachlor, butachlor, dimethenamid, propachlor, metazachlor, metolachlor, pretilachlor, thenylchlor, pethoxamid and the like],
(12) herbicidal diphenylether compounds [acifluorfen-sodium, bifenox, oxyfluorfen, lactofen, fomesafen, chlomethoxynil, aclonifen and the like],
(13) herbicidal cyclic imide compounds [oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone and the like],
(14) herbicidal pyrazole compounds [benzofenap, pyrazolate, pyrazoxyfen, topramezone, pyrasulfotole and the like],
(15) herbicidal triketone compounds [isoxaflutole, benzobicyclon, sulcotrione, mesotrione, tembotrione, tefuryltrione and the like],
(16) herbicidal aryloxyphenoxypropionate compounds [clodinafop-propargyl, cyhalofop-butyl, diclofop-methyl, fenoxaprop-ethyl, fluazifop-butyl, haloxyfop-methyl, quizalofop-ethyl, metamifop and the like],
(17) herbicidal trione oxime compounds [alloxydim-sodium, sethoxydim, butroxydim, clethodim, cloproxydim, cycloxydim, tepraloxydim, tralkoxydim, profoxydim and the like],
(18) herbicidal sulfonylurea compounds [chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron and the like],
(19) herbicidal imidazolinone compounds [imazamethabenz-methyl, imazamethapyr, imazamox, imazapyr, imazaquin, imazethapyr and the like],
(20) herbicidal sulfonamide compounds [flumetsulam, metosulam, diclosulam, florasulam, cloransulam-methyl, penoxsulam, pyroxsulam and the like],
(21) herbicidal pyrimidinyloxybenzoate compounds [pyrithiobac-sodium, bispyribac-sodium, pyriminobac-methyl, pyribenzoxim, pyriftalid, pyrimisulfan and the like],
(22) other kinds of herbicidal compounds [bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl and the like] and the like.

Active ingredients of the plant growth regulator include, for example, hymexazol, paclobutrazol, uniconazole-P, inabenfide, prohexadione-calcium and the like.
Active ingredients of the fungicide include, for example, as follows:
(1) fungicidal polyhaloalkylthio compounds [captan and the like],
(2) fungicidal organophosphorus compounds [IBP, EDDP, tolclofos-methyl and the like],
(3) fungicidal benzimidazole compounds [benomyl, carbendazim, thiophanate-methyl and the like],
(4) fungicidal carboxyamide compounds [carboxin, mepronil, flutolanil, thifluzamid, furametpyr, boscalid, penthiopyrad and the like],
(5) fungicidal dicarboxyimide compounds [procymidone, iprodione, vinclozolin and the like],
(6) fungicidal acylalanine compounds [metalaxyl and the like],
(7) fungicidal azole compounds [triadimefon, triadimenol, propiconazole, tebuconazole, cyproconazole, epoxiconazole, prothioconazole, ipconazole, triflumizole, prochloraz and the like],
(8) fungicidal morpholine compounds [dodemorph, tridemorph, fenpropimorph and the like],
(9) fungicidal strobilurin compounds [azoxystrobin, kresoxim-methyl, metominostrobin, trifloxystrobin, picoxystrobin, pyraclostrobin and the like],
(10) fungicidal antibiotics [validamycin A, blasticidin S, kasugamycin, polyoxin and the like],
(11) fungicidal dithiocarbamate compounds [mancozeb, maneb and the like],
(12) other kinds of fungicidal compounds [fthalide, probenazole, isoprothiolane, tricyclazole, pyroquilon, ferimzone, acibenzolar S-methyl, carpropamid, diclocymet, fenoxanil, tiadinil, diclomezine, teclofthalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, bordeaux mixture and the like] and the like.
Active ingredients of the insecticide include, for example, as follows:
(1) insecticidal organophosphorus compounds [fenthion, fenitrothion, pirimiphos-methyl, diazinon, quinalphos, isoxathion, pyridafenthion, chlorpyrifos-methyl, vamidothion, malathion, phenthoate, dimethoate, disulfoton, monocrotophos, tetrachlorvinphos, chlorfenvinphos, propaphos, acephate, trichlorphon, EPN, pyraclofos and the like],
(2) insecticidal carbamate compounds [carbaryl, metolcarb, isoprocarb, BPMC, propoxur, XMC, carbofuran, carbosulfan, benfuracarb, furathiocarb, methomyl, thiodicarb and the like],
(3) insecticidal synthetic pyrethroid compounds [tefluthrin, bifenthrin, cycloprothrin, ethofenprox and the like],
(4) insecticidal nereistoxin-based compounds [cartap, bensultap, thiocyclam and the like],
(5) insecticidal neonicotinoid compounds [imidacloprid, nitenpyram, acetamiprid, thiamethoxam, thiacloprid, dinotefuran, clothianidin and the like],
(6) insecticidal benzoylphenylurea compounds [chlorfluazuron, flufenoxuron, hexaflumuron, lufenuron, novaluron and the like],
(7) insecticidal macrolide compounds [emamectin, spinosad and the like],
(8) other kinds of insecticidal compounds [buprofezin, tebufenozide, fipronil, ethiprole, pymetrozine, diafenthiuron, indoxacarb, tolfenpyrad, pyridalyl, flonicamid, flubendiamide and the like] and the like.

Active ingredients of the acaricide include, for example, hexythiazox, pyridaben, fenpyroximate, tebufenpyrad, chlorfenapyr, etoxazole, pyrimidifen, acequinocyl, bifenazate, spirodiclofen and the like.

Active ingredients of the nematocide include, for example, fosthiazate, cadusafos and the like.

The herbicide which contains the present compound as an active ingredient may, if necessary, be further mixed with a safener (for example, furilazole, dichlormid, benoxacor, allidochlor, isoxadifen-ethyl, fenchlorazole-ethyl, mefenpyr-diethyl, cloquintocet-mexyl, fenclorim, cyprosulfamide, cyometrinil, oxabetrinil, fluxofenim, flurazole, 1,8-naphthalicanhydride andthe like), coloring agent, fertilizer (for example, urea and the like) and the like.

The present compound may be used as an active ingredient of herbicides for croplands such as a field, a rice paddy, a lawn, an orchard, or non-croplands. The present compound may control weeds without causing any crop injury to "crops" in a place cultivating the "crops" listed below.

"Crops"

Corn, rice, wheat, barley, rye, oats, *sorghum*, cotton, soybean, peanut, common buckwheat, sugar beet, rape, sunflower, sugar cane, tobacco and the like;

Solanaceae vegetables (eggplant, tomato, green pepper, red pepper, potato and the like), Cucurbitaceous vegetables (cucumber, pumpkin, zucchini, watermelon, melon and the like), Brassicaceae vegetables (Japanese radish, turnip, horseradish, kohlrabi, Chinese cabbage, cabbage, leaf mustard, broccoli, cauliflower and the like), Compositae vegetables (burdock, garland chrysanthemum, artichoke, lettuce and the like), Liliaceae vegetables (leek, onion, garlic, asparagus and the like), Umbelliferae vegetables (carrot, parsley, celery, wild parsnip and the like), Chenopodiaceae vegetables (spinach, Swiss chard and the like), Labiatae vegetables (perilla, mint, basil and the like), strawberry, sweet potato, yam, taro and the like;

ornamental flowers;

houseplants;

pomaceous fruits (apple, pear, Japanese pear, Chinese quince, quince and the like), stone fruits (peach, plum, nectarine, Japanese plum, mahaleb cherry, apricot, prune and the like), citrus (tangerine, orange, lemon, lime, grapefruit and the like), nuts (chestnut, walnut, hazel, almond, pistachio, cashew nut, macadamia nut and the like), sap fruits (blueberry, cranberry, blackberry, raspberry and the like), grape, persimmon, olive, loquat, banana, coffee, date palm, coconut palm and the like; and tea plant, mulberry, flowering plants, roadside trees (ash plant, birch, American dogwood, eucalyptus, ginkgo, lilac, maple, willow oak, poplar, cercis, liquidambar, plane tree, zelkova, Thuja standishii, Abies, hemlock spruce, needle juniper, pine, Norway spruce, yew) and the like.

Crops being conferred resistance to herbicides by classic breeding technique, gene recombination technology or the like are included in such "crops". There is no crop injury to the crops, to which resistance to herbicides was given, when herbicides such as HPPD inhibitors such as isoxaflutole; ALS inhibitors such as imazethapyr, thifensulfuron-methyl; EPSP synthase inhibitors; glutamine synthetase inhibitors; acetyl CoA carboxylase inhibitors; or bromoxynil and the like; are applied.

The crops to which herbicidal resistance is given by classic breeding technique include, for example, Clearfield (registered trademark) canola with resistance to imidazolinone herbicides, STS soy bean with resistance to sulfonylurea herbicides, SR corn with resistance to acetyl CoA carboxylase inhibitors. The crops, to which the resistance to acetyl CoA carboxylase inhibitors is given, are described in, for example, Proc. Natl. Acad. Sci. USA, vol. 87, pp. 7175 (1990).

In addition, mutant acetyl CoA carboxylase conferring resistance to acetyl CoA carboxylase inhibitors is described, for example, in Weed Science vol. 53, pp. 728-746 (2005). Resistance to acetyl CoA carboxylase inhibitors can be conferred to the crops when the gene coding this mutant acetyl CoA carboxylase is introduced into the crops by gene recombination technology, or when mutations related to acetyl CoA carboxylase inhibitor-resistance is introduced into the gene coding acetyl CoA carboxylase.

The "crops" to which herbicidal resistance is conferred by gene recombination technology are known (for example, corn varieties to which resistance to glyphosate or glufosinate is added). Such corn varieties are commercially available as a product name of Roundup Ready (registered trademark) or Liberty Link (registered trademark).

The "crops" include crops to which ability to produce insecticidal toxins is given by gene recombination technology.

Such insecticidal toxins include, for example, insecticidal proteins produced from *Bacillus cereus* or *Bacillus popilliae*; δ-endotoxins such as Cry1Ab, Cry1Ac, Cry1F, Cry1Fa2, Cry2Ab, Cry3A, Cry3Bb1 and Cry9C produced from *Bacillus thuringiensis*; insecticidal proteins such as VIP1, VIP2, VIP3 and VIP3A; insecticidal proteins produced from nematode; toxins produced by animals such as a scorpion toxin, a spider toxin, a bee toxin and an insect specific nervous system toxin; Filamentous fungus toxins; Plant lectins; Agglutinins; protease inhibitors such as trypsin inhibitors, serine protease inhibitors, patatin, cystatin and papain inhibitors; ribosome inactivation proteins (RIP) such as ricins, corn-RIP, abrins, saporins, bryodin; steroid metabolism enzymes such as 3-hydroxysteroid oxidase, ecdysteroid-UDP-glucosyltransferase, cholesterol oxidase; ecdysone inhibitors; HMG-CoA reductase; ion channel inhibitors such as sodium channel or calcium channel inhibitor; Juvenile hormone esterase; diuretic hormone receptors; stilbene synthase; bibenzyl synthase; chitinase; and glucanases.

The insecticidal toxins include hybrid proteins of said insecticidal proteins, insecticidal proteins in which a part of amino acids composing the proteins is deleted or substituted. Hybrid proteins are created by putting different domains of these insecticidal proteins together by gene recombination technology. For example, Cry1Ab, in which a part of amino acid is deleted, is known as the above insecticidal protein in which a part of amino acids composing the protein is deleted.

For example, insecticidal toxins and the "crops" being given an ability to produce insecticidal toxins by gene recombination technology are described in EP-A-0 374 753, WO 93/07,278, WO 95/34,656, EP-A-0 427 529, EP-A-451 878 and WO 03/052,073.

For example, the "crops" being given an ability to produce insecticidal toxins by gene recombination technology have resistance to attack from Coleopteran pests, Dipteran pests and/or Lepidopteran pests.

Examples of commercially available "crops" being given an ability to produce insecticidal toxins by gene recombination technology include YieldGard (registered trademark) (corn variety expressing Cry1Ab toxin), YieldGard Rootworm (registered trademark) (corn variety expressing Cry3Bb1 toxin), YieldGard Plus (registered trademark) (corn variety expressing Cry1Ab and Cry3Bb1 toxins), Herculex I (registered trademark) (corn variety expressing Cry1Fa2 toxin and phosphinothricin N-acetyltransferase (PAT) to confer resistance to glufosinate), NuCOTN33B (registered trademark) (cotton variety expressing Cry1Ac toxin), Bollgard I (registered trademark) (cotton variety expressing Cry1Ac toxin), Bollgard II (registered trademark) (cotton variety expressing Cry1Ac and Cry2Ab toxins), VIPCOT (registered trademark) (cotton variety expressing VIP toxin), NewLeaf (registered trademark) (potato variety expressing Cry3A toxin), NatureGard (registered trademark) Agrisure (registered trademark) GT Advantage (GA21 glyphosate resistance trait), Agrisure (registered trademark) CB Advantage (Bt11 corn borer (CB) trait) and Protecta (registered trademark).

The "crops" also include crops being given an ability to produce anti-pathogen substances by gene recombination technology.

Anti-pathogen substances include, for example, PR proteins (PRPs, described in EP-A-0 392 225); ion channel inhibitors such as sodium channel inhibitors, calcium channel inhibitors (KP1, KP4 and KP6 toxins and the like produced by virus are known); stilbene synthase; bibenzyl synthase; chitinase; glucanase; microorganism-producing substances such as peptide antibiotics, antibiotics having a heterocycle; and protein factors relating to resistance against plant pathogens (described in WO 03/000,906) and the like.

The crops being given an ability to produce an anti-pathogen substance by gene recombination technology are described, for example, in EP-A-0 392 225, WO 95/33, 818 and EP-A-0 353 191.

When the present compound is mixed with flumioxazin, the mixing ratio is preferably 0.1 to 10 by weight of flumioxazin based on 1 by weight of the present compound. The composition comprising the present compound and flumioxazin can be used for soil treatment or foliage treatment. The composition comprising the present compound and flumioxazin may control weeds without causing any crop injury in a place cultivating corn, rice, wheat, barley, rye, oats, *sorghum*, cotton, soybean, peanut, sugar beet, rape, sunflower, sugarcane and the like. And the composition comprising the present compound and flumioxazin may be used for croplands such as a lawn, an orchard, or non-croplands.

When the present compound is mixed with glyphosate, the mixing ratio is preferably 1 to 100 by weight of glyphosate based on 1 by weight of the present compound. The composition comprising the present compound and glyphosate can be used for foliage treatment. The composition comprising the present compound and glyphosate may control weeds without giving any crop injury in a place cultivating corn, rice, wheat, barley, rye, oats, *sorghum*, cotton, soy bean, peanut, sugar beet, rape, sunflower, sugarcane and the like. And the composition comprising the present compound and glyphosate may be used for croplands such as a lawn, an orchard, or non-croplands.

The present compound can be produced, for example, by following preparation methods.

Preparation Method 1

Among the present compound, the compound represented by the formula (I-a), in which G is a hydrogen atom can be produced by the reaction of the compound represented by the formula (II) with a metal hydroxide,

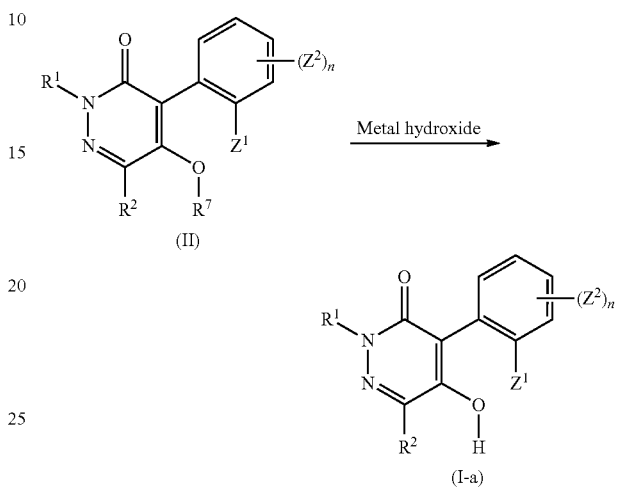

(wherein in formula, $R^7$ represents a $C_{1-6}$ alkyl group (for example, a methyl group, an ethyl group, etc.) and $R^1$, $R^2$, $Z^1$, $Z^2$ and n denote the same as the above mentioned).

The reaction is generally carried out in a solvent. The solvent used in the reaction includes, for example, water, ethers such as tetrahydrofuran, dioxane or a mixed solvent thereof.

The metal hydroxide used in the reaction includes, for example, a hydroxide of an alkali metal such as sodium hydroxide, potassium hydroxide and the like. The amount of the metal hydroxide used in the reaction is generally 1 to 120 mole equivalents, preferably 1 to 40 mole equivalents to the compound represented by the formula (II).

The reaction temperature is generally in the range of room temperature to boiling point of the solvent, preferably at a boiling point of the solvent. The reaction may be carried out by heating in a sealed tube or a high pressure resistant closed vessel. The reaction time is generally in the range from 5 minutes to a few weeks.

The completion of the reaction may be confirmed with use of an analytical means such as thin layer chromatography, high performance liquid chromatography or the like after sampling a part of the reaction mixture. After the completion of the reaction, the compound represented by the formula (I-a) may be isolated, for example, by the following operation: addition of an acid to the reaction mixture, to which water is added to mix, followed by extraction with an organic solvent to form an organic layer, which is dried and concentrated.

Preparation Method 2

Among the present compound, the compounds represented by the formula (I-b), in which G is a group except a hydrogen atom can be produced from the compound represented by the formula (I-a) and the compound represented by the formula (III),

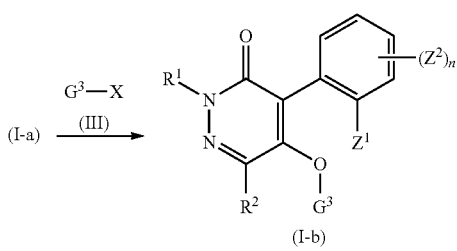

(wherein in formula, $G^3$ among G defined represents a group except a hydrogen atom, X represents a halogen atom (for example, a chlorine atom, a bromine atom, an iodine atom, etc.) or a group represented by the formula $OG^3$ and $R^1$, $R^2$, $Z^1$, $Z^2$ and n denote the same as the above mentioned).

The reaction may be carried out in a solvent. The solvent used in the reaction includes, for example, aromatic hydrocarbons such as benzene, toluene, etc., ethers such as diethyl ether, diisopropyl ether, dioxane, tetrahydrofuran, dimethoxyethane, etc., halogenated hydrocarbons such as dichloromethane, chloroform, 1,2-dichloroethane, etc., amides such as dimethylformamide, dimethylacetamide, etc., sulfoxides such as dimethylsulfoxide, etc., sulfones such as sulforane, etc. or a mixed solvent thereof.

The compound represented by the formula (III) used in the reaction includes, for example, carboxylic acid halides such as acetyl chloride, propionyl chloride, isobutyryl chloride, pivaloyl chloride, benzoyl chloride, cyclohexanecarbonyl chloride, etc., carboxylic acid anhydrides such as acetic anhydride, trifluoroacetic anhydride, etc., carbonate half ester halides such as methyl chloroformate, ethyl chloroformate, phenyl chloroformate, etc., carbamoyl halides such as dimethylcarbamoyl chloride, etc., sulfonyl halides such as methanesulfonyl chloride, p-toluenesulfonyl chloride, etc., sulfonic acid anhydrides such as methanesulfonic anhydride, trifluoromethanesulfonic anhydride, etc., or halogenated phosphate esters such as dimethyl chlorophosphate, etc. The amount of the compound represented by the formula (III) used in the reaction is generally one mole equivalent or more, preferably 1 to 3 mole equivalents to the compound represented by the formula (I-a).

The reaction is generally carried out in the presence of a base. The base used in the reaction includes, for example, organic bases such as triethylamine, tripropylamine, pyridine, dimethylaminopyridine, 1,8-diazabicyclo[5.4.0]-7-undecene, etc., and inorganic bases such as sodium hydroxide, potassium hydroxide, calcium hydroxide, sodium carbonate, potassium carbonate, sodium hydrogen carbonate, calcium carbonate, sodium hydride, etc. The amount of the base used in the reaction is generally 0.5 to 10 mole equivalents, preferably 1 to 5 mole equivalents to the compound represented by the formula (I-a).

The reaction temperature is generally at −30 to 180° C., preferably at −10 to 50° C. The reaction time is generally from 10 minutes to 30 hours.

The completion of the reaction may be confirmed with use of an analytical means such as thin layer chromatography, high performance liquid chromatography or the like after sampling a part of the reaction mixture. After the completion of the reaction, the compound represented by the formula (I-b) may be isolated, for example, by the following operation: mixing the reaction mixture with water followed by extraction with an organic solvent to form an organic layer, which is dried and concentrated.

The compound represented by the formula (III) is a known compound or may be produced from a known compound.

Preparation Method 3

Among the present compound, the compound represented by the formula (I-a), in which G is a hydrogen atom can also be produced by the following preparation method. The compound represented by the formula (I-a) can be produced by the reaction of the compound represented by the formula (VI) with a base,

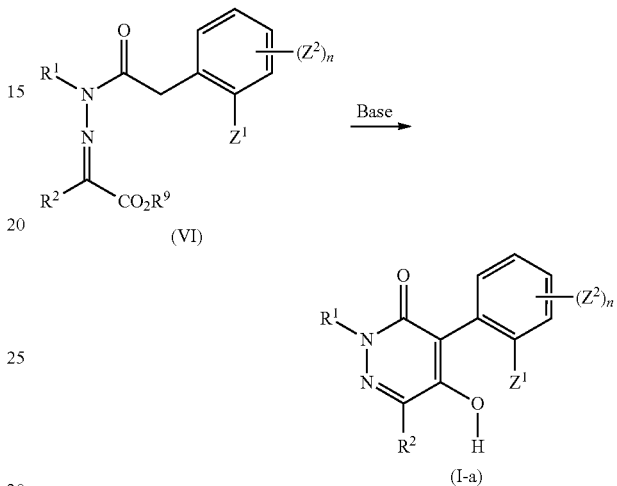

(wherein in formula, $R^9$ represents a $C_{1-6}$ alkyl group (for example, a methyl group, an ethyl group, etc.) and $R^1$, $R^2$, $Z^1$, $Z^2$ and n denote the same as the above mentioned).

The reaction is generally carried out in a solvent. The solvent used in the reaction includes, for example, aromatic hydrocarbons such as benzene, toluene, xylene, etc., ethers such as diethyl ether, diisopropyl ether, dioxane, tetrahydrofuran, dimethoxyethane, etc., halogenated hydrocarbons such as dichloromethane, chloroform, 1,2-dichloroethane, etc., amides such as dimethylformamide, dimethylacetamide, etc., sulfones such as sulforane, etc., or a mixed solvent thereof.

The base used in the reaction includes, for example, metal alkoxides such as potassium tert-butoxide, etc., alkali metal hydrides such as sodium hydride, etc., and organic bases such as triethylamine, tributylamine, N,N-diisopropylethylamine, etc. The amount of the base used in the reaction is generally 1 to 10 mole equivalents, preferably 2 to 5 mole equivalents to the compound represented by the formula (VI).

The reaction temperature is generally at −60 to 180° C., preferably at −10 to 100° C. The reaction time is generally from 10 minutes to 30 hours.

The completion of the reaction may be confirmed with use of an analytical means such as thin layer chromatography, high performance liquid chromatography or the like after sampling a part of the reaction mixture. After the completion of the reaction, the compound represented by the formula (I-a) may be isolated, for example, by the following operation: addition of an acid to the reaction mixture, to which water is added to mix, followed by extraction with an organic solvent to form an organic layer, which is dried and concentrated.

Reference Preparation Method 1

The compound represented by the formula (II) can be produced, for example, by the following preparation method,

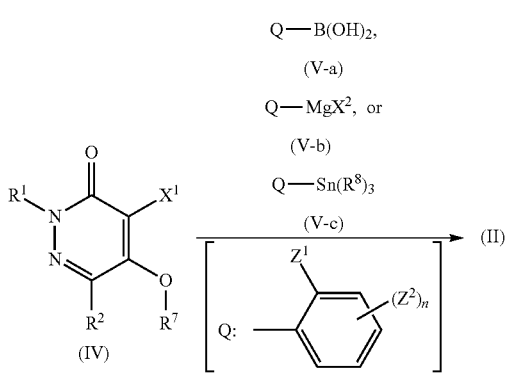

(wherein in formula, $X^1$ represents a leaving group (for example, a halogen atom such as a chlorine atom, a bromine atom, an iodine atom, etc.), $X^2$ represents a halogen atom (for example, a chlorine atom, a bromine atom, an iodine atom, etc.), $R^8$ represents a $C_{1-6}$ alkyl group (for example, a methyl group, a butyl group, etc.) and $R^1$, $R^2$, $R^7$, $Z^1$, $Z^2$ and n denote the same as the above mentioned).

The compound represented by the formula (II) can be produced by a coupling reaction of the compound represented by the formula (IV) with an organometallic reagent represented by the formulas (V-a), (V-b) or (V-c) (generally one mole equivalent or more, preferably 1 to 3 mole equivalents to the compound represented by the formula (IV)).

When the compound represented by the formula (V-a) is used, said coupling reaction is carried out in a solvent. The solvent used in the reaction includes, for example, aromatic hydrocarbons such as benzene, toluene, etc., alcohols such as methanol, ethanol, propanol, etc., ethers such as diethyl ether, diisopropyl ether, dioxane, tetrahydrofuran, dimethoxyethane, etc., ketones such as acetone, methyl ethyl ketone, etc., amides such as dimethylformamide, dimethylacetamide, etc., sulfoxides such as dimethylsulfoxide, etc., sulfones such as sulfolane, etc., water or a mixed solvent thereof.

When the compound represented by the formula (V-a) is used, said coupling reaction is carried out in the presence of a base. The base used in the reaction includes, for example, organic bases such as triethylamine, tripropylamine, pyridine, dimethylaniline, dimethylaminopyridine, 1,8-diazabicyclo[5.4.0]-7-undecene, etc., and inorganic bases such as sodium hydroxide, potassium hydroxide, calcium hydroxide, sodium carbonate, potassium carbonate, sodium hydrogen carbonate, calcium carbonate, cesium carbonate, potassium phosphate, etc. The amount of the base used in the reaction is generally 0.5 to 10 mole equivalents, preferably 1 to 5 mole equivalents to the compound represented by the formula (IV).

Furthermore, when the compound represented by the formula (V-a) is used, said coupling reaction is carried out in the presence of a catalyst. The catalyst used in the reaction includes, for example, a palladium catalyst such as tetrakis(triphenylphosphine)palladium, dichlorobis(triphenylphosphine)palladium, etc. The amount of the catalyst used in the reaction is generally 0.001 to 0.5 mole equivalent, preferably 0.01 to 0.2 mole equivalent to the compound represented by the formula (IV). When the compound represented by the formula (V-a) is used, a quaternary ammonium salt is preferably added in said coupling reaction. The quaternary ammonium salt used includes, for example, tetrabutylammonium bromide, etc.

When the compound represented by the formula (V-a) is used, a reaction temperature of said coupling reaction is generally at 20 to 180° C., preferably at 60 to 150° C. The reaction time is generally from 30 minutes to 100 hours.

The completion of the reaction may be confirmed with use of an analytical means such as thin layer chromatography, high performance liquid chromatography or the like after sampling a part of the reaction mixture. After the completion of the reaction, the compound represented by the formula (II) may be isolated, for example, by the following operation: mixing the reaction mixture with water, followed by extraction with an organic solvent to form an organic layer, which is dried and concentrated.

When the compound represented by the formula (V-b) is used, said coupling reaction is carried out in a solvent. The solvent used in the reaction includes, for example, aromatic hydrocarbons such as benzene, toluene, etc., ethers such as diethyl ether, diisopropyl ether, dioxane, tetrahydrofuran, dimethoxyethane, etc., or a mixed solvent thereof.

When the compound represented by the formula (V-b) is used, said coupling reaction is carried out in the presence of a catalyst. The catalyst used in the reaction includes, for example, a nickel catalyst such as dichlorobis(1,3-diphenylphosphino)propanenickel, dichlorobis(triphenylphosphine)nickel, etc., and a palladium catalyst such as tetrakis(triphenylphosphine)palladium, dichlorobis(triphenylphosphine)palladium, etc. The amount of the catalyst used in the reaction is generally 0.001 to 0.5 mole equivalent, preferably 0.01 to 0.2 mole equivalent to the compound represented by the formula (IV).

When the compound represented by the formula (V-b) is used, the reaction temperature of said coupling reaction is generally at −80 to 180° C., preferably at −30 to 150° C. The reaction time is generally from 30 minutes to 100 hours.

The completion of the reaction may be confirmed with use of an analytical means such as thin layer chromatography, high performance liquid chromatography or others after sampling a part of the reaction mixture. After the completion of the reaction, the compound represented by the formula (II) may be isolated, for example, by the following operation: mixing the reaction mixture with water, followed by extraction with an organic solvent to form an organic layer, which is dried and concentrated.

When the compound represented by the formula (V-c) is used, said coupling reaction is carried out in a solvent. The solvent used in the reaction includes, for example, aromatic hydrocarbons such as benzene, toluene, etc., ethers such as diethyl ether, diisopropyl ether, dioxane, tetrahydrofuran, dimethoxyethane, etc., halogenated hydrocarbons such as chloroform, 1,2-dichloroethane, etc., amides such as dimethylformamide, dimethylacetamide, etc., or a mixed solvent thereof.

When the compound represented by the formula (V-c) is used, said coupling reaction is carried out in the presence of a catalyst. The catalyst used in the reaction includes, for example, a palladium catalyst such as tetrakis(triphenylphosphine)palladium, dichlorobis(triphenylphosphine)palladium, etc. The amount of the catalyst used in the reaction is generally 0.001 to 0.5 mole equivalent, preferably 0.01 to 0.2 mole equivalent to the compound represented by the formula (IV).

When the compound represented by the formula (V-c) is used, the reaction temperature of said coupling reaction is generally at −80 to 180° C., preferably at −30 to 150° C. The reaction time is generally from 30 minutes to 100 hours.

The completion of the reaction may be confirmed with use of an analytical means such as thin layer chromatography, high performance liquid chromatography or others after sampling a part of the reaction mixture. After the completion of the reaction, the compound represented by the formula (II) may be isolated, for example, by the following operation: mixing the reaction mixture with water, followed by extraction with an organic solvent to form an organic layer, which is dried and concentrated.

The compound represented by the formula (II) can be produced, for example, by a method in accordance with the one described in Tetrahedron vol. 57, pp 1323-1330 (2001), etc.

Organometallic reagents represented by the formulas (V-a), (V-b) and (V-c) are known compounds or can be produced by methods in accordance with known methods using known compounds.

The compound represented by the formula (IV) is a known compound or can be produced using known compounds. The compound can be produced, for example, by a method described in J. Heterocycl. Chem., vol. 33, pp 1579-1582 (1996) and the like, or a method in accordance with the one thereof.

Reference Preparation Method 2

The compound represented by the formula (VI) can be produced, for example, by a following preparation method, The amount of the compound represented by the formula (VIII) used in the reaction is generally 1 mole equivalent or more, preferably 1 to 3 mole equivalents to the compound represented by the formula (VII). The amount of a base used in the reaction is generally 0.5 to 10 mole equivalents, preferably 1 to 5 mole equivalents to the compound represented by the formula (VII).

The reaction temperature is generally at −30 to 180° C., preferably at −10 to 50° C. The reaction time is generally from 10 minutes to 30 hours.

The completion of the reaction may be confirmed with use of an analytical means such as thin layer chromatography, high performance liquid chromatography or the like after sampling a part of the reaction mixture. After the completion of the reaction, the compound represented by the formula (VI) may be isolated, for example, by the following operation: mixing the reaction mixture with water, followed by extraction with an organic solvent to form an organic layer, which is dried and concentrated.

The compound represented by the formula (VII) can be produced by the reaction of the compound represented by the formula (IX)

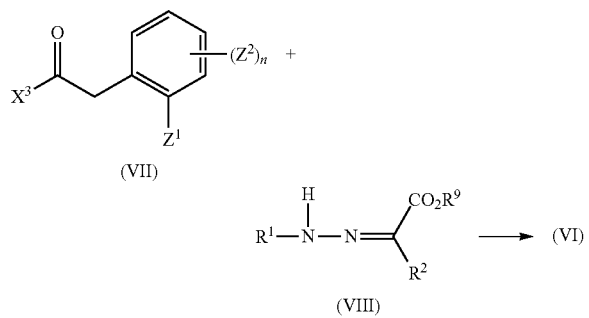

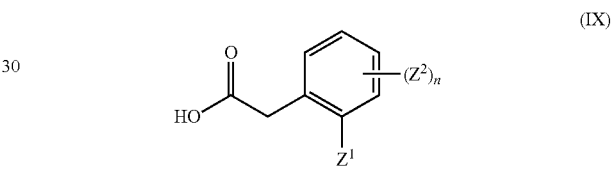

(wherein in formula, $Z^1$, $Z^2$ and n denote the same as the above mentioned)

with a halogenation reagent (for example, thionyl chloride, thionyl bromide, phosphorous oxychloride, oxalyl chloride, etc.).

The compound represented by the formula (IX) is a known compound or can be produced from known compounds. The compound can be produced, for example, according to methods described in Organic Syntheses Collective Volume 3, pp 557-560 (1955), J. Am. Chem. Soc. Vol. 63, pp 2643-2644 (1941) and WO 2006/056282, etc., and methods similar to them. The compound represented by the formula (IX) includes, for example, 2,4,6-trimethylphenyl acetic acid, 2,4,6-triethylphenylacetic acid, 2,6-diethyl-4-methylphenylacetic acid, 2-ethylphenylacetic 2-ethyl-4,6-dimethylphenylacetic acid, 2,4-diethylphenylacetic acid, 2,6-diethylphenylacetic acid, 2,6-diethyl-6-methylphenylacetic acid, etc.

The compound represented by the formula (VIII) is a known compound or can be produced from known compounds.

Each compound produced by above mentioned Preparation method 1 to 3 or Reference preparation method 1 to 2 may be isolated and/or purified by known procedures, for example, concentration, concentration under reduced pressure, extraction, transference dissolution, crystallization, re-crystallization, chromatography and the like.

Next, specific examples of the present compound are shown below.

(wherein in formula, $X^3$ represents a halogen atom (for example, a chlorine atom, a bromine atom, an iodine atom, etc.) and $R^1$, $R^2$, $R^9$, $Z^1$, $Z^2$ and n denote the same as the above mentioned).

The reaction is generally carried out in a solvent. The solvent used in the reaction includes, for example, nitriles such as acetonitrile, etc., ketones such as acetone, etc., aromatic hydrocarbons such as benzene, toluene, etc., ethers such as diethyl ether, diisopropyl ether, dioxane, tetrahydrofuran, dimethoxyethane, etc., halogenated hydrocarbons such as dichloromethane, chloroform, 1,2-dichloroethane, etc., amides such as dimethylformamide, dimethylacetamide, etc., sulfones such as sulfolane, etc., or a mixed solvent thereof.

The reaction of the compound represented by the formula (VII) with the compound represented by the formula (VIII) is generally carried out in the presence of a base. The base used in the reaction includes, for example, organic bases such as triethylamine, tripropylamine, pyridine, dimethylaminopyridine, 1,8-diazabicyclo[5.4.0]-7-undecene, 1,4-diazabicyclo[2.2.2]octane, etc., and inorganic bases such as sodium hydroxide, potassium hydroxide, calcium hydroxide, sodium carbonate, potassium carbonate, sodium hydrogen carbonate, calcium carbonate, sodium hydride, etc.

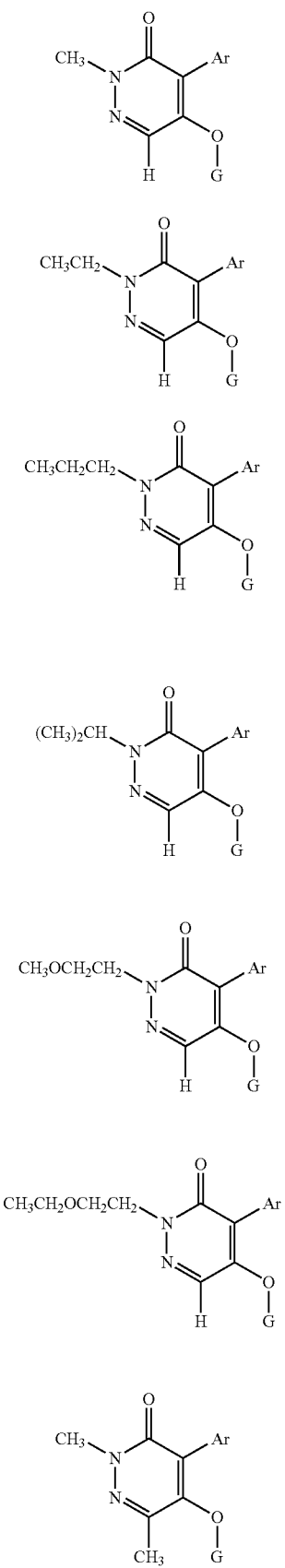
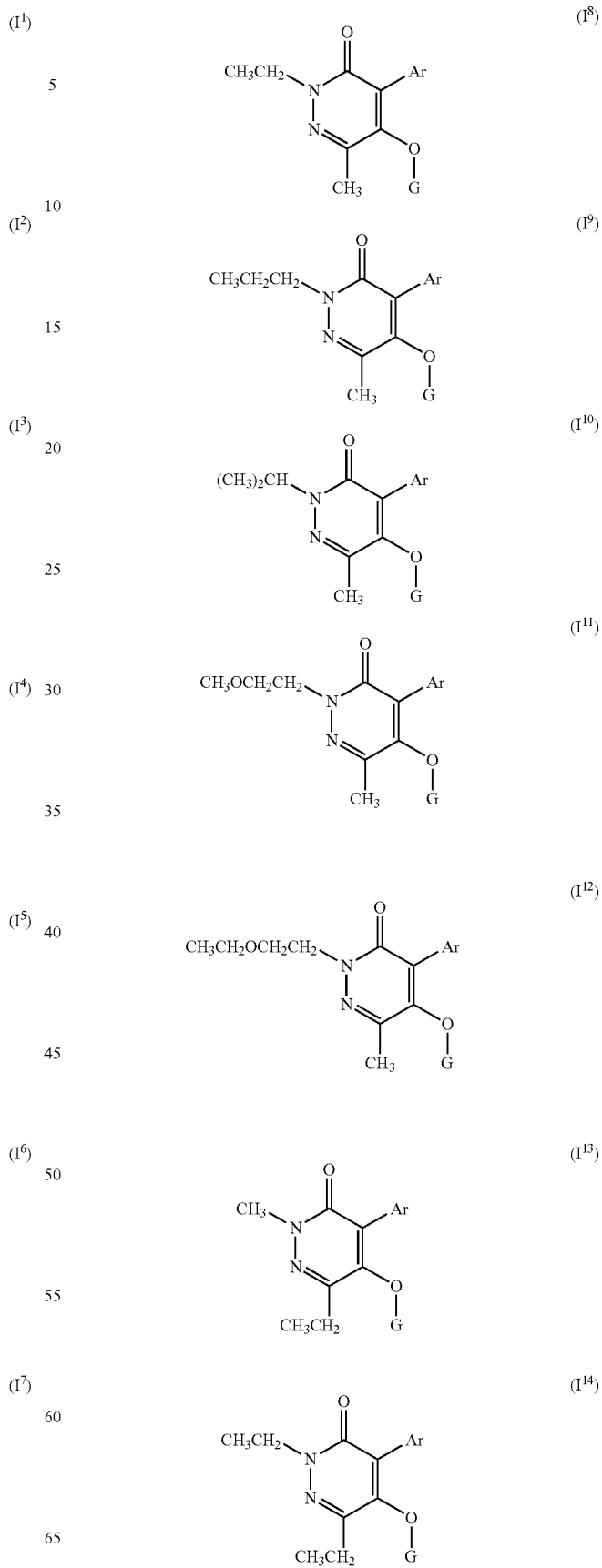

-continued
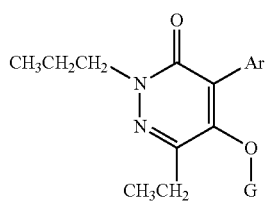
(I¹⁵)
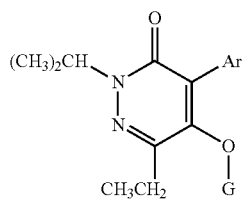
(I¹⁶)
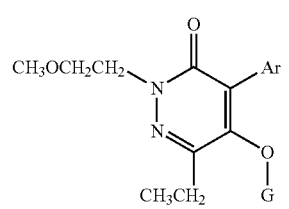
(I¹⁷)
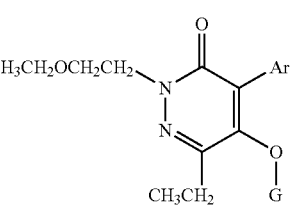
(I¹⁸)
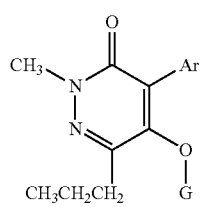
(I¹⁹)
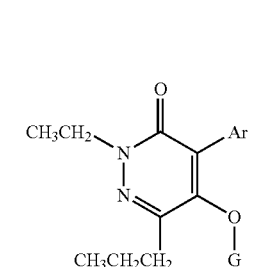
(I²⁰)
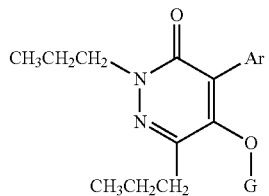
(I²¹)
-continued
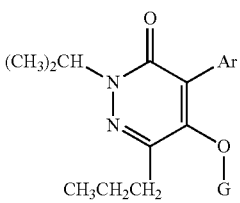
(I²²)
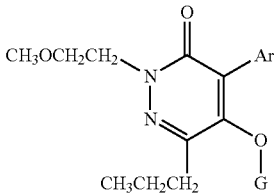
(I²³)
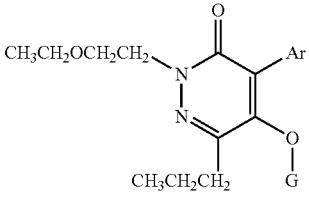
(I²⁴)
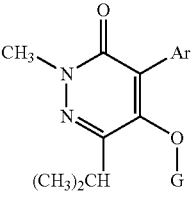
(I²⁵)
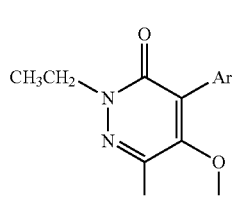
(I²⁶)
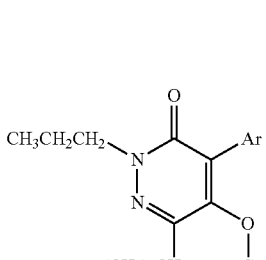
(I²⁷)
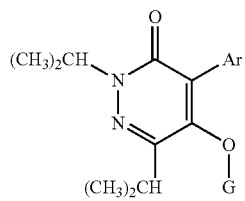
(I²⁸)

-continued (I²⁹)

CH₃OCH₂CH₂—N, Ar, (CH₃)₂CH, O, G (pyridazinone structure)

(I³⁰)

CH₃CH₂OCH₂CH₂—N, Ar, (CH₃)₂CH, O, G (pyridazinone structure)

(1) The pyridazinone compound wherein Ar is a 2-ethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(2) The pyridazinone compound wherein Ar is a 2-propylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(3) The pyridazinone compound wherein Ar is a 2,4-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(4) The pyridazinone compound wherein Ar is a 2,6-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(5) The pyridazinone compound wherein Ar is a 2-ethyl-4-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(6) The pyridazinone compound wherein Ar is a 2-ethyl-6-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(7) The pyridazinone compound wherein Ar is a 2,6-diethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(8) The pyridazinone compound wherein Ar is a 2,4,6-trimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(9) The pyridazinone compound wherein Ar is a 2-ethyl-4,6-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(10) The pyridazinone compound wherein Ar is a 2,6-diethyl-4-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(11) The pyridazinone compound wherein Ar is a 2,4,6-triethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(12) The pyridazinone compound wherein Ar is a 2,4-diethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^1$) to ($I^{30}$).

(13) The pyridazinone compound wherein Ar is a 2,4-diethyl-6-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group in any of the formula ($I^2$) to ($I^{30}$).

The embodiments of the compound represented by the formula (II) include, for example, the following embodiments among the above defined the compound represented by the formula (II).

The compound in the formula (II), wherein n is an integer of 1 or more.

The compound in the formula (II), wherein n is 0 and $Z^1$ is a $C_{2-6}$ alkyl group.

The compound in the formula (II), wherein n is 1 or 2 and $Z^2$ is (a) substituent(s) on 4- and/or 6-position of the benzene ring.

The compound in the formula (II), wherein $R^1$ is a $C_{1-3}$ alkyl group or a ($C_{1-3}$ alkyloxy) $C_{1-3}$ alkyl group.

The compound in the formula (II), wherein $R^2$ is a hydrogen atom or a $C_{1-3}$ alkyl group.

The compound in the formula (II), wherein $R^2$ is a hydrogen atom or a methyl group.

The compound in the formula (II), wherein $Z^1$ is a $C_{1-3}$ alkyl group and $Z^2$ is a $C_{1-3}$ alkyl group.

The compound in the formula (II), wherein $R^2$ is a $C_{1-3}$ alkyl group or a ($C_{1-3}$ alkyloxy) $C_{1-3}$ alkyl group and $R^2$ is a hydrogen atom or a methyl group.

The compound in the formula (II), wherein $R^1$ is a $C_{1-3}$ alkyl group or a ($C_{1-3}$ alkyloxy) $C_{1-3}$ alkyl group and $R^2$ is a hydrogen atom or a $C_{1-3}$ alkyl group,
n represents 0, 1, or 2 and each of $Z^2$ may be same or different when n represents 2,
and when n represents 1 or 2, $Z^2$ is (a) substituent(s) on 4- and/or 6-position of a benzene ring,
$Z^1$ is a $C_{1-6}$ alkyl group (preferably a $C_{1-3}$ alkyl group) and
$Z^2$ is a $C_{1-6}$ alkyl group (preferably a $C_{1-3}$ alkyl group).

The compound in the formula (II), wherein $R^1$ is a $C_{1-3}$ alkyl group or a ($C_{1-3}$ alkyloxy) $C_{1-3}$ alkyl group and $R^2$ is a hydrogen atom or a methyl group,
n represents 0, 1, or 2 and each of $Z^2$ may be same or different when n represents 2,
and when n represents 1 or 2, $Z^2$ is (a) substituent(s) on 4- and/or 6-position of a benzene ring,
$Z^1$ is a $C_{1-6}$ alkyl group (preferably a $C_{1-3}$ alkyl group) and
$Z^2$ is a $C_{1-6}$ alkyl group (preferably a $C_{1-3}$ alkyl group).

The embodiments of the compound represented by the formula (VI) include, for example, the following embodiments among the above defined the compound represented by the formula (VI).

The compound in the formula (VI), wherein n is an integer of 1 or more.

The compound in the formula (VI), wherein n is 0 and $Z^1$ is a $C_{2-6}$ alkyl group.

The compound in the formula (VI), wherein n is 1 or 2 and $Z^2$ is (a) substituent(s) on 4- and/or 6-position of the benzene ring.

The compound in the formula (VI), wherein $R^1$ is a $C_{1-3}$ alkyl group or a ($C_{1-3}$ alkyloxy) $C_{1-3}$ alkyl group.

The compound in the formula (VI), wherein $R^2$ is a $C_{1-6}$ alkyl group.

The compound in the formula (VI), wherein $R^2$ is a hydrogen atom or a $C_{1-3}$ alkyl group.

The compound in the formula (VI), wherein $R^2$ is a $C_{1-3}$ alkyl group.

The compound in the formula (VI), wherein $R^2$ is a hydrogen atom or a methyl group.

The compound in the formula (VI), wherein $R^2$ is a methyl group.

The compound in the formula (VI), wherein $Z^1$ is a $C_{1-3}$ alkyl group and $Z^2$ is a $C_{1-3}$ alkyl group.

The compound in the formula (VI), wherein $R^1$ is a $C_{1-3}$ alkyl group or a ($C_{1-3}$ alkyloxy) $C_{1-3}$ alkyl group and $R^2$ is a hydrogen atom or a methyl group.

The compound in the formula (VI), wherein $R^1$ is a $C_{1-3}$ alkyl group or a ($C_{1-3}$ alkyloxy) $C_{1-3}$ alkyl group and $R^2$ is a hydrogen atom or a $C_{1-3}$ alkyl group,
n represents 0, 1, or 2 and each of $Z^2$ may be same or different when n represents 2,
and when n represents 1 or 2, $Z^2$ is (a) substituent(s) on 4- and/or 6-position of a benzene ring,
$Z^1$ is a $C_{1-6}$ alkyl group (preferably a $C_{1-3}$ alkyl group) and
$Z^2$ is a $C_{1-6}$ alkyl group (preferably a $C_{1-3}$ alkyl group).

The compound in the formula (VI), wherein $R^1$ is a $C_{1-3}$ alkyl group or a ($C_{1-3}$ alkyloxy) $C_{1-3}$ alkyl group and $R^2$ is a hydrogen atom or a methyl group,
n represents 0, 1, or 2 and each of $Z^2$ may be same or different when n represents 2,
and when n represents 1 or 2, $Z^2$ is (a) substituent(s) on 4- and/or 6-position of a benzene ring,
$Z^1$ is a $C_{1-6}$ alkyl group (preferably a $C_{1-3}$ alkyl group) and
$Z^2$ is a $C_{1-6}$ alkyl group (preferably a $C_{1-3}$ alkyl group).

The present invention will be further illustrated by the following Examples, Reference examples, Formulation examples and Test examples; however the present invention is not limited to these examples.

In the Examples and Reference examples, room temperature means usually 10 to 30° C. $^1$H-NMR means proton nuclear magnetic resonance. It is measured with tetramethyl silane as internal standard, and chemical shift (δ) is shown by ppm.

The abbreviations used in the Examples and Reference examples have the following meanings:
$CDCl_3$: Chloroform-d, s: singlet, d: doublet, t: triplet, q: quartet, dt: doublet triplet, dq: doublet quartet, m: multiplet, br.: broad, J: coupling constant, Me: methyl group, Et: ethyl group, Pr: propyl group, i-Pr: isopropyl group, t-Bu: tert-butyl group, c-Hex: cyclohexyl group and Ph: phenyl group.

EXAMPLE 1

4-(2-Ethylphenyl)-5-hydroxy-2-methyl-3(2H)-pyridazinone (Compound I-a-1)

After 50 mL of water, 4.657 g of potassium hydroxide (content, 85%) and 5 mL of 1,4-dioxane were added to 3.193 g of 4-(2-ethylphenyl)-5-methoxy-2-methyl-3(2H)-pyridazinone (Compound II-1), the mixture was stirred and heated under reflux for 36 hours. After cooling, concentrated hydrochloric acid was added to the reaction mixture to acidify, to which 10 ml of water and 100 ml of ethyl acetate were added. The resulting mixture was filtered to remove insoluble substances and the filtrate was separate to two phase. The organic layer was washed with water and then a saturated sodium chloride aqueous solution and dried over anhydrous magnesium sulfate, and the solvent was distilled off. The solid obtained was washed with a mixed solvent of ethyl acetate and hexane (1:2) to yield 2.050 g of the title compound as colorless crystals.

The present compound which was produced according to Example 1 will be shown in Table 1.

The compound represented by the formula (I-a):

TABLE 1

(I-a)

$$\text{structure with } R^1\text{-N, N, } R^2, \text{OH, } Z^1, (Z^2)_n$$

| Compound | $R^1$ | $R^2$ | $Z^1$ | $(Z^2)_n$ | m.p./° C. |
|---|---|---|---|---|---|
| I-a-1 | Me | H | Et | — | 218-220 |
| I-a-2 | Et | H | Et | — | 190-192 |
| I-a-3 | i-Pr | H | Et | — | 226-227 |
| I-a-4 | MeOCH$_2$CH$_2$ | H | Et | — | 137-139 |
| I-a-5 | Me | H | Pr | — | 210-211 |
| I-a-6 | Me | H | Me | 6-Me | 267-271 |
| I-a-7 | Me | H | Et | 6-Me | 239-242 |
| I-a-8 | Me | H | Et | 6-Et | 247-249 |
| I-a-9 | Me | H | Me | 4-Me | 219-220 |
| I-a-10 | Me | H | Me | 4-Me, 6-Me | 272-275 |
| I-a-11 | Et | H | Me | 4-Me, 6-Me | >300 |
| I-a-12 | Me | H | Et | 4-Me, 6-Et | 254-255 |

EXAMPLE 2

4-(2,6-Diethyl-4-methylphenyl)-5-hydroxy-2,6-dimethyl-3(2H)-pyridazinone (Compound I-a-14)

Under a nitrogen atmosphere, 13 mL of a tetrahydrofuran solution of potassium tert-butoxide (1 mol/L) was stirred at room temperature, to which a solution of 1.9 g of ethyl 2-[2-(2,6-diethyl-4-methylphenylacetyl)-2-methylhydrazono]propanoate (Compound VI-2) in 55 mL of toluene was added dropwise over about 1 hour. The mixture was further stirred at room temperature for 30 minutes. Then, the reaction mixture was concentrated under reduced pressure. To the residue obtained was added 30 mL of ice-water, which was extracted with tert-butyl methyl ether (20 mL×2). To the aqueous layer was then added 1.6 g of 35% hydrochloric acid, which was extracted with ethyl acetate (20 mL×3). The ethyl acetate extracts were combined, washed with saturated sodium chloride aqueous solution (20 mL×2), dried over anhydrous magnesium sulfate and concentrated under reduced pressure. The residue obtained was subjected to a silica gel column chromatography (ethyl acetate:hexane=1:3 as eluent) to yield 0.76 g of a solid. The solid was washed with cold hexane and air-dried to yield 0.59 g of the title compound as white powder.

The present compound which was produced according to Example 2 will be shown in Table 2.

The compound represented by the formula (I-a):

TABLE 2

(I-a)

$$\text{structure with } R^1\text{-N, N, } R^2, \text{OH, } Z^1, (Z^2)_n$$

| Compound | $R^1$ | $R^2$ | $Z^1$ | $(Z^2)_n$ | m.p./° C. |
|---|---|---|---|---|---|
| I-a-13 | Me | Me | Me | 4-Me, 6-Me | 199-201 |
| I-a-14 | Me | Me | Et | 4-Me, 6-Et | 205-206 |
| I-a-15 | Me | Me | Et | — | 171-172 |
| I-a-16 | Me | Me | Et | 4-Me | 187-188 |
| I-a-17 | Me | Me | Et | 4-Et, 6-Et | 188-190 |
| I-a-18 | Me | Me | Et | 4-Me, 6-Me | 176-177 |
| I-a-19 | Me | Et | Et | 4-Me, 6-Et | 194-195 |
| I-a-20 | Me | Et | Et | 4-Me | 148-149 |
| I-a-21 | Me | Et | Et | 4-Me, 6-Me | 188-189 |
| I-a-22 | Me | Et | Me | 4-Me, 6-Me | 210-211 |
| I-a-23 | Me | i-Pr | Et | 4-Me, 6-Me | 208-210 |
| I-a-24 | Me | Pr | Et | 4-Me, 6-Et | 175-176 |
| I-a-25 | Me | Et | Et | 4-Et, 6-Et | 170-171 |
| I-a-26 | Me | Pr | Et | 4-Et, 6-Et | 174-175 |
| I-a-27 | Me | Me | Et | 4-Et | 178-180 |
| I-a-28 | Me | Et | Et | 4-Et | 163-164 |
| I-a-29 | Me | Me | Et | 4-Et, 6-Me | 168-169 |
| I-a-30 | Me | Me | Et | 6-Et | 187-188 |

EXAMPLE 3

5-Benzoyloxy-4-(2-ethylphenyl)-2-methyl-3(2H)-pyridazinone (Compound I-b-1)

To 0.326 g of Compound I-a-1 were added 12 mL of tetrahydrofuran and 0.40 mL of triethylamine. The mixture obtained was chilled with ice, to which 0.25 mL of benzoyl chloride was further added. The mixture was stirred for 10 minutes under cooling with ice and then at room temperature for 3 hours. 30 mL of water was added to the reaction mixture, which was extracted with 30 mL of ethyl acetate twice. The extracts were combined, washed with a saturated sodium chloride aqueous solution and dried over anhydrous magnesium sulfate, and the solvent was distilled off. The residue was subjected to a silica gel column chromatography (as eluent, ethyl acetate:hexane=1:2, and then 2:1) to yield 0.463 g of the title compound as colorless oil.

The present compound which was produced according to Example 3 will be shown in Table 3.

The compound represented by the formula (I-b):

TABLE 3

(I-b)

$$\text{Structure with } R^1, R^2, Z^1, (Z^2)_n, G^3 \text{ substituents on pyridazinone core}$$

| Compound | $R^1$ | $R^2$ | $Z^1$ | $(Z^2)_n$ | $G^3$ | m.p./° C. |
|---|---|---|---|---|---|---|
| I-b-1 | Me | H | Et | — | COPh | * |
| I-b-2 | Me | H | Et | — | COMe | 69-70 |
| I-b-3 | Me | H | Et | — | COEt | * |
| I-b-4 | Me | H | Et | — | CO i-Pr | 77-79 |
| I-b-5 | Me | H | Et | — | CO t-Bu | 56-59 |
| I-b-6 | Me | H | Et | — | CO c-Hex | * |
| I-b-7 | Me | H | Et | — | $CO_2Me$ | 81-82 |
| I-b-8 | Me | H | Et | — | $CONMe_2$ | * |
| I-b-9 | Me | H | Et | — | $SO_2Me$ | * |
| I-b-10 | Me | H | Pr | — | COMe | 78-79 |
| I-b-11 | Me | H | Me | 4-Me, 6-Me | CO t-Bu | 93-96 |
| I-b-12 | Me | H | Et | 4-Me, 6-Et | COMe | 99-101 |
| I-b-13 | Me | Me | Me | 4-Me, 6-Me | COMe | 130-131 |
| I-b-14 | Me | Me | Et | 4-Me, 6-Et | COMe | 133-134 |
| I-b-15 | Me | Me | Et | 4-Me, 6-Et | CO t-Bu | 105-106 |
| I-b-16 | Me | Me | Et | — | COMe | 148-149 |
| I-b-17 | Me | Me | Et | — | CO t-Bu | 89 |
| I-b-18 | Me | Me | Et | 4-Me, 6-Et | $CO_2Et$ | 73-74 |
| I-b-19 | Me | Me | Et | 4-Me, 6-Et | COPh | 145-146 |
| I-b-20 | Me | Me | Et | 4-Me | COMe | 142-143 |
| I-b-21 | Me | Me | Et | 4-Et, 6-Et | COMe | 103-104 |
| I-b-22 | Me | Me | Et | 4-Me, 6-Me | COMe | 106-107 |
| I-b-23 | Me | Me | Et | 4-Me, 6-Et | COEt | 103-104 |
| I-b-24 | Me | Me | Et | 4-Me, 6-Et | CO i-Pr | 102-103 |
| I-b-25 | Me | Me | Et | 4-Me, 6-Et | $CO_2Me$ | 95-96 |
| I-b-26 | Me | Me | Et | 4-Me, 6-Et | $CO_2Ph$ | 105 |
| I-b-27 | Me | Me | Et | 4-Me, 6-Et | $SO_2Me$ | 153-154 |
| I-b-28 | Me | Me | Et | 4-Me, 6-Et | $SO_2CF_3$ | 63-67 |
| I-b-29 | Me | Et | Et | 4-Me, 6-Et | COMe | 133-134 |
| I-b-30 | Me | Pr | Et | 4-Me, 6-Et | COMe | 161-162 |
| I-b-31 | Me | i-Pr | Et | 4-Me, 6-Et | COMe | 159-160 |
| I-b-32 | Me | Et | Et | 4-Et, 6-Et | COMe | 117-118 |
| I-b-33 | Me | Me | Et | 4-Et | COMe | 115-116 |

Concerning the compound which is marked with * in the column m.p. of Table 3, $^1$H-NMR data will be shown below.

Compound I-b-1:
$^1$H-NMR (CDCl$_3$) δ ppm: 1.14 (3H, t, J=7.7 Hz), 2.45-2.62 (2H, m), 3.88 (3H, s), 7.09-7.12 (1H, m), 7.15-7.20 (1H, m), 7.28-7.30 (2H, m), 7.37-7.42 (2H, m), 7.55-7.60 (1H, m), 7.81-7.84 (2H, m), 7.95 (1H, s).

Compound I-b-3:
$^1$H-NMR (CDCl$_3$) δ ppm: 0.94 (3H, t, J=7.6 Hz), 1.13 (3H, t, J=7.7 Hz), 2.27 (2H, dq, J=1.4, 7.6 Hz), 2.38-2.56 (2H, m), 3.84 (3H, s), 7.00-7.03 (1H, m), 7.18-7.23 (1H, m), 7.30-7.35 (2H, m), 7.75 (1H, s).

Compound I-b-6:
$^1$H-NMR (CDCl$_3$) δ ppm: 1.13 (3H, t, J=7.7 Hz), 1.10-1.22 (5H, m), 1.5-1.7 (5H, m), 2.28 (1H, br.), 2.38-2.55 (2H, m), 3.84 (3H, s), 6.99-7.02 (1H, m), 7.17-7.22 (1H, m), 7.29-7.36 (2H, m), 7.72 (1H, s).

Compound I-b-8:
$^1$H-NMR (CDCl$_3$) δ ppm: 1.11 (3H, t, J=7.7 Hz), 2.40-2.57 (2H, m), 2.64 (3H, s), 2.85 (3H, s), 3.83 (3H, s), 7.05-7.08 (1H, m), 7.19-7.24 (1H, m), 7.30-7.36 (2H, m), 7.95 (1H, s).

Compound I-b-9:
$^1$H-NMR (CDCl$_3$) δ ppm: 1.18 (3H, t, J=7.6 Hz), 2.43-2.57 (2H, m), 2.58 (3H, s), 3.85 (3H, s), 7.16-7.19 (1H, m), 7.25-7.30 (1H, m), 7.36-7.43 (2H, m), 7.96 (1H, s).

A typical example of the preparation of the compound represented by the formula (II) is shown in Reference example 1.

REFERENCE EXAMPLE 1

4-(2-Ethylphenyl)-5-methoxy-2-methyl-3 (2H)-pyridazinone (Compound II-1)

To a mixture of 2.516 g of 4-chloro-5-methoxy-2-methyl-3 (2H)-pyridazinone, 2.575 g of 2-ethylphenylboronic acid and 3.333 g of sodium carbonate were added 30 mL of 1,4-dioxane and 20 mL of water. To the mixture were added 2.417 g of tetrabutylammonium bromide and 0.657 g of tetrakis (triphenylphosphine)palladium, and then under a nitrogen atmosphere, the resulting mixture was stirred and heated under reflux for 17 hours. After cooling, 50 mL of water was added to the reaction mixture, which was extracted with 100 mL of ethyl acetate and then 30 mL of ethyl acetate. The extracts were combined, washed with a saturated sodium chloride aqueous solution and dried over anhydrous magnesium sulfate, and the solvent was distilled off. The solid obtained was washed with a mixed solvent of ethyl acetate and hexane (1:2) to yield 3.238 g of the title compound as yellow crystals.

The compound which was produced according to Reference example 1 will be shown in Table 4.

The compound represented by the formula (II):

TABLE 4

(II)

| Compound | $R^1$ | $R^2$ | $Z^1$ | $(Z^2)_n$ | $R^7$ | m.p./° C. |
|---|---|---|---|---|---|---|
| II-1 | Me | H | Et | — | Me | 127-130 |
| II-2 | Et | H | Et | — | Me | * |
| II-3 | i-Pr | H | Et | — | Me | 121-123 |
| II-4 | MeOCH$_2$CH$_2$ | H | Et | — | Me | * |
| II-5 | Me | H | Pr | — | Me | 86-88 |
| II-6 | Me | H | Me | 6-Me | Me | 187-189 |
| II-7 | Me | H | Et | 6-Me | Me | * |
| II-8 | Me | H | Et | 6-Et | Me | 165-166 |
| II-9 | Me | H | Me | 4-Me | Me | 141-142 |
| II-10 | Me | H | Me | 4-Me, 6-Me | Me | 186-192 |
| II-11 | Et | H | Me | 4-Me, 6-Me | Me | 100-102 |
| II-12 | Me | H | Et | 4-Me, 6-Et | Me | 147-149 |

Concerning the compound which is marked with * in the column m.p. of Table 4, $^1$H-NMR data will be shown below.

Compound II-2:
$^1$H-NMR (CDCl$_3$) δ ppm: 1.12 (3H, t, J=7.7 Hz), 1.39 (3H, t, J=7.3 Hz), 2.40-2.53 (2H, m), 3.81 (3H, s), 4.19-4.30 (2H, m), 7.10 (1H, d, J=7.6 Hz), 7.21-7.26 (1H, m), 7.30-7.33 (2H, m), 7.88 (1H, s).

Compound II-4:
$^1$H-NMR (CDCl$_3$) δ ppm: 1.12 (3H, t, J=7.7 Hz), 2.38-2.52 (2H, m), 3.38 (3H, s), 3.82 (3H, s), 3.77-3.84 (2H, m), 4.40

(2H, t, J=5.6 Hz), 7.11 (1H, d, J=7.6 Hz), 7.21-7.26 (1H, m), 7.30-7.34 (2H, m), 7.90 (1H, s).

Compound II-7:

$^1$H-NMR (CDCl$_3$) δ ppm: 1.08 (3H, t, J=7.7 Hz), 2.07 (3H, s), 2.30-2.45 (2H, m), 3.81 (3H, s), 3.82 (3H, s), 7.10 (1H, d, J=7.6 Hz), 7.13 (1H, d, J=7.6 Hz), 7.24 (1H, t, J=7.6 Hz), 7.85 (1H, s).

A typical example of the preparation of the compound represented by the formula (V-a) is shown in Reference example 2.

REFERENCE EXAMPLE 2

2-Propylphenylboronic acid 15.5 mL of butyl lithium (1.6 mol/L solution in hexane) was placed in a reaction vessel, which was chilled in a dry ice-acetone bath. To this was added a solution of 4.412 g of 2-propylbromobenzene in 45 mL of tetrahydrofuran at −70° C. dropwise over 85 minutes under a nitrogen atmosphere. The mixture was stirred at −70° C. for 30 minutes, to which 3.75 mL of trimethyl borate was then added at −70° C. dropwise over 15 minutes. The mixture was stirred at −70° C. for one hour and then at room temperature for 18 hours. To the reaction mixture was added 33 mL of 2N hydrochloric acid dropwise over 10 minutes and then the mixture was stirred at room temperature for 4 hours. To the mixture was added 20 mL of water, which was extracted with 70 mL of ethyl acetate. The extract was washed with a saturated sodium chloride aqueous solution and dried over anhydrous magnesium sulfate, and the solvent was distilled off. The residue was subjected to a silica gel column chromatography (as eluent, ethyl acetate:hexane=1:2, and then 2:1) to yield 1.641 g of the title compound as colorless crystals.

$^1$H-NMR (CDCl$_3$) δ ppm: 1.01 (3H, t, J=7.4 Hz), 1.69-1.79 (2H, m), 3.15-3.20 (2H, m), 4.0-6.0 (2H, br.), 7.28-7.33 (2H, m), 7.47 (1H, dt, J=1.5, 7.6 Hz), 8.20-8.23 (1H, m).

Among the compounds represented by the formula (V-a), the following ones were produced by the manner similar to Reference example 2.

2-Ethyl-6-methylphenylboronic acid m.p.: 90-91° C.

$^1$H-NMR (CDCl$_3$) δ ppm: 1.22 (3H, t, J=7.6 Hz), 2.35 (3H, s), 2.64 (2H, q, J=7.6 Hz), 4.0-5.5 (2H, br.), 6.98 (1H, d, J=7.7 Hz), 7.01 (1H, d, J=7.7 Hz), 7.18 (1H, t, J=7.7 Hz).

2,6-Diethyl-4-methylphenylboronic acid m.p.: 111-113° C.

$^1$H-NMR (CDCl$_3$) δ ppm: 1.23 (6H, t, J=7.7 Hz), 2.31 (3H, s), 2.63 (4H, q, J=7.7 Hz), 4.0-5.0 (2H, br.), 6.88 (2H, s).

A typical example of the preparation of the compound represented by the formula (VI) is shown in Reference example 3.

REFERENCE EXAMPLE 3

Ethyl 2-[2-(2,6-diethyl-4-methylphenylacetyl)-2-methylhydrazono]propanoate (Compound VI-2)

1.5 g of potassium carbonate was added to a solution of 2.0 g of ethyl 2-(methylhydrazono)propanoate in 35 mL of acetonitrile. The mixture was stirred under cooling with ice, to which a solution of 2.6 g of 2,6-diethyl-4-methylphenylacetyl chloride in 10 mL of acetonitrile was added dropwise over about 20 minutes. The resulting mixture was further stirred for 3.5 hours at room temperature, and then concentrated under reduced pressure. To the residue obtained was added 20 mL of ice-water, which was extracted with ethyl acetate (20 mL×3). The extracts were combined, washed with a saturated sodium chloride aqueous solution (20 mL×2), dried over anhydrous magnesium sulfate and concentrated under reduced pressure. The residue obtained was subjected to basic alumina column chromatography (ethyl acetate:hexane=1:3 as eluent) to yield 1.9 g of the title compound as white crystals.

The compound which was produced according to Reference example 3 will be shown in Table 5.

The compound represented by the formula (VI):

TABLE 5

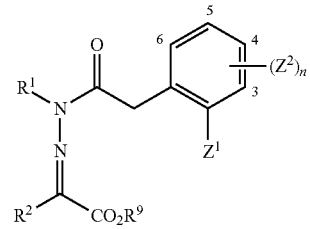

(VI)

| Compound | R$^1$ | R$^2$ | Z$^1$ | (Z$^2$)$_n$ | R$^9$ | m.p./° C. |
|---|---|---|---|---|---|---|
| VI-1 | Me | Me | Me | 4-Me, 6-Me | Et | 90-91 |
| VI-2 | Me | Me | Et | 4-Me, 6-Et | Et | 73-76 |
| VI-3 | Me | Me | Et | — | Et | * |
| VI-4 | Me | Me | Et | 4-Me | Et | * |
| VI-5 | Me | Me | Et | 4-Et, 6-Et | Et | 63-66 |
| VI-6 | Me | Me | Et | 4-Me, 6-Me | Et | * |
| VI-7 | Me | Et | Et | 4-Me, 6-Et | Et | * |
| VI-8 | Me | Et | Et | 4-Me | Et | * |
| VI-9 | Me | Et | Et | 4-Me, 6-Me | Et | * |
| VI-10 | Me | Et | Me | 4-Me, 6-Me | Et | * |
| VI-11 | Me | i-Pr | Et | 4-Me, 6-Et | Et | * |
| VI-12 | Me | Pr | Et | 4-Me, 6-Et | Et | * |
| VI-13 | Me | Et | Et | 4-Et, 6-Et | Et | * |
| VI-14 | Me | Pr | Et | 4-Et, 6-Et | Et | * |
| VI-15 | Me | Me | Et | 4-Et | Et | * |
| VI-16 | Me | Et | Et | 4-Et | Et | * |
| VI-17 | Me | Me | Et | 4-Et, 6-Me | Et | * |
| VI-18 | Me | Me | Et | 6-Et | Et | * |

Concerning the compound which is marked with * in the column m.p. of Table 5, $^1$H-NMR data will be shown below.

Compound VI-3:

$^1$H-NMR (CDCl$_3$) δ ppm: 1.19 (3H, t, J=7.6 Hz), 1.37 (3H, t, J=7.2 Hz), 2.20 (3H, br. s), 2.67 (2H, q, J=7.7 Hz), 3.37 (3H, br. s), 4.03 (2H, br. s), 4.33 (2H, q, J=7.0 Hz), 7.06-7.30 (4H, m).

Compound VI-4:

$^1$H-NMR (CDCl$_3$) δ ppm: 1.18 (3H, t, J=7.6 Hz), 1.37 (3H, t, J=7.2 Hz), 2.20 (3H, br. s), 2.30 (3H, s), 2.63 (2H, q, J=7.7 Hz), 3.36 (3H, br. s), 3.99 (2H, br. s), 4.33 (2H, q, J=7.1 Hz), 6.93 (1H, br. d, J=7.1 Hz), 7.00 (1H, br. s), 7.12 (1H, br. d, J=7.8 Hz).

Compound VI-6:

$^1$H-NMR (CDCl$_3$) δ ppm: 1.16 (3H, t, J=7.7 Hz), 1.36 (3H, t, J=7.2 Hz), 2.22 (3H, s), 2.27 (3H, s), 2.30 (3H, br. s), 2.56 (2H, q, J=7.7 Hz), 3.39 (3H, br. s), 4.02 (2H, br. s), 4.32 (2H, q, J=7.1 Hz), 6.86 (2H, br. s).

Compound VI-7 (E/Z Mixture):

$^1$H-NMR (CDCl$_3$) δ ppm: 1.13-1.25 (9H, m), 1.31-1.41 (3H, m), 2.29 (3H, s), 2.50-2.81 (6H, m), 3.23, 3.43 (3H, each br. s), 4.05 (2H, br. s), 4.27-4.39 (2H, m), 6.89 (2H, s).

Compound VI-8 (E/Z Mixture):
  $^1$H-NMR (CDCl$_3$) δ ppm: 1.06-1.22 (6H, m), 1.31-1.40 (3H, m), 2.30, 2.31 (3H, each s), 2.50-2.70 (4H, m), 3.22, 3.38 (3H, each s), 4.00 (2H, br. s), 4.27-4.37 (2H, m), 6.90-6.98 (1H, m), 6.98-7.02 (1H, m), 7.02-7.14 (1H, m).

Compound VI-9 (E/Z Mixture):
  $^1$H-NMR (CDCl$_3$) δ ppm: 1.12-1.25 (6H, m), 1.31-1.41 (3H, m), 2.22 (3H, s), 2.27 (3H, s), 2.50-2.81 (4H, m), 3.23, 3.43 (3H, each br. s), 4.02 (2H, br. s), 4.26-4.37 (2H, m), 6.87 (2H, br. s).

Compound VI-10 (E/Z Mixture):
  $^1$H-NMR (CDCl$_3$) δ ppm: 1.16-1.24 (3H, m), 1.32-1.40 (3H, m), 2.22 (6H, s), 2.25 (3H, s), 2.55-2.80 (2H, m), 3.23, 3.43 (3H, each br. s), 4.00 (2H, br. s), 4.27-4.38 (2H, m), 6.85 (2H, s).

Compound VI-11:
  $^1$H-NMR (CDCl$_3$) δ ppm: 1.18 (6H, t, J=7.6 Hz), 1.24 (6H, d, J=6.8 Hz), 1.37 (3H, t, J=7.1 Hz), 2.29 (3H, s), 2.55 (4H, q, J=7.6 Hz), 2.85 (1H, septet, J=6.8 Hz), 3.22 (3H, s), 4.04 (2H, s), 4.34 (2H, q, J=7.2 Hz), 6.88 (2H, s).

Compound VI-12 (E/Z Mixture):
  $^1$H-NMR (CDCl$_3$) δ ppm: 1.01 (3H, t, J=7.4 Hz), 1.17 (6H, t, J=7.6 Hz), 1.31-1.40 (3H, m), 1.57-1.74 (2H, m), 2.30 (3H, s), 2.50-2.76 (6H, m), 3.22, 3.42 (3H, each s), 4.03, 4.05 (2H, each br. s), 4.26-4.36 (2H, m), 6.89 (2H, s).

Compound VI-13 (E/Z mixture):
  $^1$H-NMR (CDCl$_3$) δ ppm: 1.13-1.28 (12H, m), 1.30-1.40 (3H, m), 2.50-2.80 (8H, m), 3.23, 3.44 (3H, each s), 4.06 (2H, br. s), 4.28-4.39 (2H, m), 6.91 (2H, s).

Compound VI-14 (E/Z Mixture):
  $^1$H-NMR (CDCl$_3$) δ ppm: 1.01 (3H, br. t, J=7.2 Hz), 1.13-1.26 (9H, m), 1.30-1.40 (3H, m), 1.56-1.73 (2H, m), 2.50-2.76 (8H, m), 3.22, 3.42 (3H, each s), 4.03, 4.06 (2H, each br. s), 4.26-4.37 (2H, m), 6.91 (2H, s).

Compound VI-15:
  $^1$H-NMR (CDCl$_3$) δ ppm: 1.15-1.25 (6H, m), 1.37 (3H, t, J=7.2 Hz), 2.20 (3H, br. s), 2.55-2.70 (4H, m), 3.36 (3H, br. s), 3.99 (2H, br. s), 4.33 (2H, q, J=7.1 Hz), 6.96 (1H, br. d, J=7.3 Hz), 7.02 (1H, br. s), 7.15 (1H, br. d, J=7.8 Hz).

Compound VI-16 (E/Z Mixture):
  $^1$H-NMR (CDCl$_3$) δ ppm: 1.05-1.25 (9H, m), 1.32-1.40 (3H, m), 2.50-2.69 (6H, m), 3.22, 3.38 (3H, each s), 4.00 (2H, br. s), 4.26-4.36 (2H, m), 6.93-7.00 (1H, m), 7.00-7.04 (1H, m), 7.06-7.18 (1H, m).

Compound VI-17:
  $^1$H-NMR (CDCl$_3$) δ ppm: 1.17 (3H, t, J=7.6 Hz), 1.22 (3H, t, J=7.6 Hz), 1.36 (3H, t, J=7.1 Hz), 2.24 (3H, s), 2.30 (3H, br. s), 2.58 (4H, q, J=7.6 Hz), 3.40 (3H, br. s), 4.03 (2H, br. s), 4.32 (2H, q, J=7.2 Hz), 6.89 (2H, s).

Compound VI-18:
  $^1$H-NMR (CDCl$_3$) δ ppm: 1.19 (6H, t, J=7.6 Hz), 1.36 (3H, t, J=7.2 Hz), 2.32 (3H, br. s), 2.60 (4H, q, J=7.7 Hz), 3.40 (3H, br. s), 4.09 (2H, br. s), 4.33 (2H, q, J=7.2 Hz), 7.07 (2H, d, J=7.6 Hz), 7.18 (1H, t, J=7.6 Hz).

FORMULATION EXAMPLE 1

| Emulsifiable concentrate | |
|---|---|
| Compound I-a-1 | 20% by weight |
| polyoxyethylene alkyl ether | 5% by weight |
| dimethylformamide | 18% by weight and |
| xylene | 57% by weight | are mixed to yield an emulsifiable concentrate. The emulsifiable concentrate prepared is used after properly diluted with water. Compounds I-a-2 to I-a-23 and I-b-1 to I-b-23 instead of Compound I-a-1 are similarly formulated to yield the emulsifiable concentrate for each compound.

FORMULATION EXAMPLE 2

| Wettable powder | |
|---|---|
| Compound I-b-2 | 50% by weight |
| sodium lignin sulfonate | 5% by weight |
| polyoxyethylene alkyl ether | 5% by weight |
| white carbon | 5% by weight and |
| clay | 35% by weight | are pulverized and mixed to yield wettable powder. The wettable powder prepared is used after properly diluted with water.

FORMULATION EXAMPLE 3

| Granule | |
|---|---|
| Compound I-a-12 | 1.5% by weight |
| sodium lignin sulfonate | 2% by weight |
| talc | 40% by weight and |
| bentonite | 56.5% by weight | are mixed, kneaded with water and palletized to yield granules.

FORMULATION EXAMPLE 4

Ten parts of Compound (I-a-12), 10 parts of any one of the compound selected from the following Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

Group A 2,4-PA, MCP, MCPB, phenothiol, mecoprop, fluroxypyr, triclopyr, clomeprop, naproanilide, 2,3,6-TBA, dicamba, clopyralid, picloram, aminopyralid, quinclorac, quinmerac, diuron, linuron, chlortoluron, isoproturon, fluometuron, isouron, tebuthiuron, methabenzthiazuron, cumyluron, daimuron, methyl-daimuron, atrazine, ametoryn, cyanazine, simazine, propazine, simetryn, dimethametryn, prometryn, metribuzin, triaziflam, paraquat, diquat, bromoxynil, ioxynil, pendimethalin, prodiamine, trifluralin, amiprofos-methyl, butamifos, bensulide, piperophos, anilofos, glyphosate, glufosinate, bialaphos, di-allate, tri-allate, EPIC, butylate, benthiocarb, esprocarb, molinate, dimepiperate, swep, chlorpropham, phenmedipham, phenisopham, pyributicarb, asulam, propanil, propyzamide, bromobutide, etobenzanid, acetochlor, alachlor, butachlor, dimethenamid, propachlor, metazachlor, metolachlor, pretilachlor, thenylchlor, pethoxamid, acifluorfen-sodium, bifenox, oxyfluorfen, lactofen, fomesafen, chlomethoxynil, aclonifen, oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, benzofenap, pyrazolate, pyrazoxyfen, topramezone, pyrasulfotole, isoxaflutole, benzobicyclon, sulcotrione, mesotrione, tembotrione, tefuryltrione, clodinafop-propargyl, cyhalofop-butyl, diclofop-methyl, fenoxaprop-ethyl, fluazifop-butyl, haloxyfop-methyl, quizalofop-ethyl, metamifop, alloxydim-sodium, sethoxydim, butroxydim, clethodim, cloproxydim, cycloxydim, tepraloxydim, tralkoxydim, profoxydim, chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, imazamethabenz-methyl, imazamethapyr, imazamox, imazapyr, imazaquin, imazethapyr, orthosulfamuron, flucetosulfuron, flumetsulam, metosulam, diclosulam, florasulam, cloransulam-methyl, penoxsulam, pyroxsulam, pyrithiobac-sodium, bispyribac-sodium, pyriminobac-methyl, pyribenzoxim, pyriftalid, pyrimisulfan, bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, furilazole, dichlormid, benoxacor, allidochlor, isoxadifen-ethyl, fenchlorazole-ethyl, mefenpyr-diethyl, cloquintocet-mexyl, fenclorim, cyprosulfamide, cyometrinil, oxabetrinil, fluxofenim, flurazole and 1,8-naphthalic anhydride.

FORMULATION EXAMPLE 5

Ten parts of Compound (I-a-13), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 6

Ten parts of Compound (I-a-14), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 7

Ten parts of Compound (I-a-15), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 8

Ten parts of Compound (I-a-16), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 9

Ten parts of Compound (I-a-17), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 10

Ten parts of Compound (I-a-18), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 11

Ten parts of Compound (I-a-19), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 12

Ten parts of Compound (I-b-12), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 13

Ten parts of Compound (I-b-14), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 14

Ten parts of Compound (I-b-16), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 15

Ten parts of Compound (I-b-18), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 16

Ten parts of Compound (I-b-19), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 17

Ten parts of Compound (I-b-20), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 18

Ten parts of Compound (I-b-21), 10 parts of any one of the compound selected from the above-mentioned Group A, 4 parts of sodium laurylsulfate, 2 parts of calcium ligninsulfonate, 20 parts of synthetic hydrated silica and 54 parts of diatomaceous earth are pulverized and mixed well to give each wettable powders.

FORMULATION EXAMPLE 19

Ten parts of each of Compound (I-a-12), (I-a-13), (I-a-14), (I-a-15), (I-a-16), (I-a-17), (I-a-18), (I-a-19), (I-b-12), (I-b-14), (I-b-16), (I-b-18), (I-b-19), (I-b-20) or (I-b-21); 10 parts of flumioxazine; 4 parts of sodium laurylsulfate; 2 parts of calcium ligninsulfonate; 20 parts of synthetic hydrated silica and 54 parts of diatomaceous earth are pulverized and mixed well to give each wettable powders.

FORMULATION EXAMPLE 20

Five parts of each of Compound (I-a-12), (I-a-13), (I-a-14), (I-a-15), (I-a-16), (I-a-17), (I-a-18), (I-a-19), (I-b-12), (I-b-14), (I-b-16), (I-b-18), (I-b-19), (I-b-20) or (I-b-21); 25 parts of glyphosate; 4 parts of sodium laurylsulfate; 2 parts of calcium ligninsulfonate; 20 parts of synthetic hydrated silica and 44 parts of diatomaceous earth are pulverized and mixed well to give each wettable powders.

TEST EXAMPLE 1

Post-Emergence Treatment Test in Dry Field

A plastic cup with a diameter of 8 cm and a depth of 6.5 cm was filled with commercially available soil, onto which seeds of *Lolium multiflorum* were sowed, covered with soil about 0.5 cm high and then grown in a greenhouse. When the plants were grown in first to second leaf stage, a prescribed dosage of a dilute liquid formulation comprising Compound I-a-1 was sprayed to whole plants uniformly. The dilute liquid formulation was prepared by dissolving a prescribed amount of Compound I-a-1 in a dimethylformamide solution (2%) of Tween 20 (polyoxyethylene sorbitan fatty acid ester, from MP Biomedicals, Inc.) and then diluting with deionized water. The plants after treatment with the liquid formulation were grown in a greenhouse and 20 days after the treatment, the efficacy of the compound against *Lolium multiflorum* was visually evaluated by rating in eleven levels from 0 to 10 (assigned as 0 for no effect and 10 for complete death while values falling in between these values were rated from 1 to 9 levels accordingly).

The other present compounds and Compound A described in J. Heterocycl. Chem., vol. 42, pp. 427-435 (2005) as a comparative example were similarly tested.

Comparative Example (Compound A)

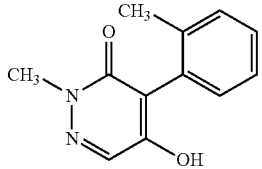

As a result, Compounds I-a-1, I-a-5, I-a-6, I-a-7, I-a-8, I-a-9, I-a-12, I-b-1, I-b-2, I-b-4, I-b-5, I-b-7, I-b-10 and I-b-11 showed the effect equal to 7 or more at a treatment dosage of 500 g/ha, whereas Compounds I-a-13, I-a-14, I-a-15, I-a-16, I-a-17, I-a-18, I-a-19, I-a-20, I-a-21, I-a-22, I-a-27, I-b-12, I-b-13, I-b-14, I-b-16, I-b-17, I-b-18, I-b-20, I-b-21, I-b-22, I-b-23 and I-b-25 showed the effect equal to 7 or more at a treatment dosage of 250 g/ha. By contrary, Compound A showed the effect to be 1 at a treatment dosage of 500 g/ha.

TEST EXAMPLE 2

Pre-Emergence Treatment Test in Dry Field

A plastic container (32 cm×22 cm×8 cm in height) was filled with soil sterilized by steam, onto which seeds of *Apera spica-venti* were sowed and covered with soil about 0.5 cm high. A prescribed dosage of a dilute liquid formulation comprising Compound I-a-1 was sprayed to the soil surface uniformly. The dilute liquid formulation was prepared by the method similar to that in Test example 1. The plants after treatment with the liquid formulation were grown in a greenhouse and three weeks after the treatment, the efficacy of the compound against *Apera spica-venti* was visually evaluated by rating in eleven levels from 0 to 10 similarly to Test example 1.

The other present compounds and Compound A as a comparative example were similarly tested.

As a result, Compounds I-a-1, I-a-2, I-a-4, I-a-5, I-a-6, I-a-8, I-a-9, I-a-10, I-b-1, I-b-5, I-b-6, I-b-7 and I-b-11 showed the effect equal to 8 or more at a treatment dosage of 500 g/ha, whereas Compounds I-a-12, I-a-13, I-a-14, I-a-15, I-a-16, I-a-17, I-a-18, I-a-19, I-a-20, I-a-21, I-a-22, I-a-23, I-b-13, I-b-14, I-b-16, I-b-18, I-b-19, I-b-20, I-b-21, I-b-22 and I-b-23 showed the effect equal to 8 or more at a treatment dosage of 250 g/ha. By contrary, Compound A showed the effect to be 1 at a treatment dosage of 500 g/ha.

INDUSTRIAL APPLICABILITY

The present compound has an excellent effect on weed control and is useful as an active ingredient of herbicides.

The invention claimed is:

1. A compound represented by the formula (II):

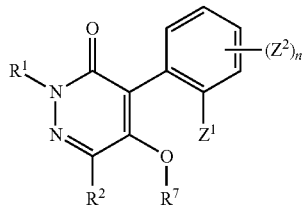

wherein in the formula, $R^1$ represents a $C_{1-6}$ alkyl group or a $(C_{1-6}$ alkyloxy) $C_{1-6}$ alkyl group,
$R^2$ represents a $C_{1-6}$ alkyl group,
$Z^1$ represents a $C_{1-6}$ alkyl group,
$Z^2$ represents a $C_{1-6}$ alkyl group, n represents 0, 1, 2, 3 or 4 and each of $Z^2$ may be same or different when n represents an integer of 2 or more,
and a sum of the number of carbon atoms in the group represented by $Z^1$ and that in the group represented by $Z^2$ is equal to 2 or more, and
$R^7$ represents a $C_{1-6}$ alkyl group.

2. The pyridazinone compound according to claim 1, wherein n is an integer equal to 1 or more.

3. The pyridazinone compound according to claim 1, wherein n is 0 and $Z^1$ is a $C_{2-6}$ alkyl group.

4. The pyridazinone compound according to claim 1, wherein n is 1 or 2 and $Z^2$ is (a) substituent(s) on 4- and/or 6-position of a benzene ring.

5. The pyridazinone compound according to claim 1, wherein $Z^1$ is a $C_{1-3}$ alkyl group and $Z^2$ is a $C_{1-3}$ alkyl group.

6. The pyridazinone compound according to claim 1, wherein $R^2$ is a $C_{1-3}$ alkyl group.

7. The pyridazinone compound according to claim 1, wherein $R^2$ is a methyl group.

8. The pyridazinone compound according to claim 1, wherein $R^1$ is a $C_{1-3}$ alkyl group or a $(C_{1-3}$ alkyloxy) $C_{1-3}$ alkyl group.

* * * * *